(12) United States Patent
Kaminski

(10) Patent No.: US 10,010,259 B2
(45) Date of Patent: Jul. 3, 2018

(54) EMG CIRCUIT

(71) Applicant: Brian E. Kaminski, Raleigh, NC (US)

(72) Inventor: Brian E. Kaminski, Raleigh, NC (US)

(73) Assignee: ADVANCER TECHNOLOGIES, LLC, Raleigh, NC (US)

( * ) Notice: Subject to any disclaimer, the term of this patent is extended or adjusted under 35 U.S.C. 154(b) by 404 days.

(21) Appl. No.: 14/701,630

(22) Filed: May 1, 2015

(65) Prior Publication Data
US 2016/0317058 A1    Nov. 3, 2016

(51) Int. Cl.
*A61B 5/04* (2006.01)
*A61B 5/0488* (2006.01)
*A61B 5/00* (2006.01)
*A61B 5/0492* (2006.01)

(52) U.S. Cl.
CPC ........ *A61B 5/0488* (2013.01); *A61B 5/04004* (2013.01); *A61B 5/7225* (2013.01); *A61B 5/04012* (2013.01); *A61B 5/0492* (2013.01); *A61B 5/742* (2013.01)

(58) Field of Classification Search
CPC . A61B 5/0488; A61B 5/04004; A61B 5/7225; A61B 5/04012; A61B 5/0492
See application file for complete search history.

(56) References Cited

U.S. PATENT DOCUMENTS

| | | | |
|---|---|---|---|
| 4,170,225 A | * | 10/1979 | Criglar ............... A61B 5/04017 482/900 |
| 4,467,813 A | * | 8/1984 | Schomburg ........ A61B 5/04004 128/902 |
| 4,540,000 A | * | 9/1985 | Doherty ............. A61B 5/04004 600/509 |
| 4,807,642 A | | 2/1989 | Brown |
| 4,811,742 A | | 3/1989 | Hassel et al. |
| 6,289,245 B1 | | 9/2001 | Mo et al. |
| 6,411,843 B1 | | 6/2002 | Zarychta |

(Continued)

OTHER PUBLICATIONS

AB Electronics UK. "Raspberry Pi expansion boards and accessories." 2014, pp. 1-2. [Retrieved on Jul. 17, 2015], Retrieved from Internet: https://www.abelectronics.co.uk/.

(Continued)

*Primary Examiner* — Devin Henson
(74) *Attorney, Agent, or Firm* — Carlson, Gaskey & Olds, P.C.

(57) ABSTRACT

According to one aspect of the present disclosure, an electromyography (EMG) circuit comprises a difference circuit, rectification circuit, offset removal circuit, and integration circuit. The difference circuit is configured to create an EMG signal based on a difference between two action potential voltages. Creation of the EMG signal introduces a voltage offset, not already present in the action potential voltages, that centers the EMG signal about a non-zero voltage. The rectification circuit is connected to the difference circuit and is configured to rectify the EMG signal about the non-zero voltage to create a rectified EMG signal. The offset removal circuit is configured to remove the voltage offset from the rectified EMG signal to create an adjusted EMG signal. The integration circuit is connected to the offset removal circuit and is configured to integrate the adjusted EMG signal to produce a first EMG output signal for a client device.

38 Claims, 13 Drawing Sheets

(56) References Cited

U.S. PATENT DOCUMENTS

| | | | |
|---|---|---|---|
| 6,532,383 B2 | 3/2003 | Maloney et al. | |
| 7,286,871 B2 | 10/2007 | Cohen | |
| 7,809,435 B1 | 10/2010 | Ettare et al. | |
| 7,896,807 B2 | 3/2011 | Clancy et al. | |
| 8,170,656 B2 | 5/2012 | Tan et al. | |
| 8,386,026 B2 | 2/2013 | Fink et al. | |
| 8,386,244 B2 | 2/2013 | Ricci et al. | |
| 2008/0200827 A1 | 8/2008 | Cyphery et al. | |
| 2009/0292194 A1* | 11/2009 | Libbus | A61B 5/0002 600/391 |
| 2011/0251512 A1 | 10/2011 | Fink et al. | |
| 2014/0275748 A1 | 9/2014 | Dunki-Jacobs et al. | |
| 2014/0309547 A1 | 10/2014 | Linderman | |
| 2015/0045689 A1 | 2/2015 | Barone | |
| 2015/0155912 A1* | 6/2015 | Winward | A61B 5/0215 375/257 |

OTHER PUBLICATIONS

Freetronics Pty Ltd. "Stacking Arduino Shields." 2010-2015, pp. 1-3 (156). [Retrieved on Jul. 17, 2015], Retrieved from Internet: http://www.freetronics.com.au/pages/stacking-arduino-shields#.ValYRfm6daR.

* cited by examiner

EMG CIRCUIT

TECHNICAL FIELD

This application relates to electromyography (EMG), and more particularly to methods and apparatus for processing producing EMG signals from action potential voltages.

BACKGROUND

Electromyography (EMG) refers to evaluating electrical activity produced by skeletal muscles. In particular, EMG measures action potential voltages that neurologically activate muscles. The action potential voltages can be measured from surface electrodes, or intramuscular electrodes that are inserted into a subject's muscle. EMG can be used for therapeutic uses, such as for physical therapy or rehabilitation. EMG has also been used for entertainment, for controlling a video game, for example.

SUMMARY

According to one aspect of the present disclosure, an electromyography (EMG) circuit is disclosed that comprises a difference circuit, rectification circuit, offset removal circuit, and an integration circuit. The difference circuit is configured to create an EMG signal based on a difference between two action potential voltages. Creation of the EMG signal introduces a voltage offset, not already present in the action potential voltages, that centers the EMG signal about a non-zero voltage. The rectification circuit is connected to the difference circuit and is configured to rectify the EMG signal about the non-zero voltage to create a rectified EMG signal. The offset removal circuit is connected to the rectification circuit and is configured to remove the voltage offset from the rectified EMG signal to create an adjusted EMG signal. The integration circuit is connected to the offset removal circuit and is configured to integrate the adjusted EMG signal to produce a first EMG output signal for a client device.

In one or more embodiments, a power supply that powers the EMG circuit provides a voltage Vs to the EMG circuit, and the non-zero voltage about which the rectification circuit rectifies the EMG signal is Vs/2.

In the same or other embodiments, the EMG circuit includes an output that provides the EMG signal, prior to the rectification, as a second EMG output signal to the same or another client device.

In one or more of the embodiments above, the voltage offset introduced by the difference circuit is a first voltage offset, the action potential voltages include a second voltage offset prior to the creation of the EMG signal, and the EMG circuit includes an additional offset removal circuit configured to remove the second voltage offset from the EMG signal prior to the rectification. In some such embodiments, the additional offset removal circuit is a high-pass filter.

In one or more of the embodiments above, the EMG circuit includes a light-emitting diode (LED) configured such that the first EMG output signal passes through the LED, and a luminance of the LED varies based on an amplitude of the first EMG output signal.

In one or more of the embodiments above, the EMG circuit includes a circuit board, a first electrode receptacle, and a second electrode receptacle. The circuit board supports one or more of the difference circuit, rectification circuit, offset removal circuit, and integration circuit. In some such embodiments, the circuit board has first and second openings that are spaced apart from each other on the circuit board, and the circuit board lies within a first plane. The first electrode receptacle is sized to receive a corresponding first electrode extension, and includes an inlet having a centerline that extends through the first electrode receptacle and is perpendicular to the first plane. The second electrode receptacle is sized to receive a corresponding second electrode extension, and includes an inlet having a centerline that extends through the second electrode receptacle and is perpendicular to the first plane. In some such embodiments, the first and second electrode receptacles are snap-in electrode receptacles, the first electrode receptacle is embedded in the first opening, and the second electrode receptacle is embedded in the second opening. In some such embodiments, the EMG circuit includes a third electrode receptacle that is mounted to the circuit board and is sized to receive a third electrode extension, wherein the third electrode receptacle has a centerline that extends parallel to the first plane.

In one or more of the embodiments above, the two action potential voltages comprise a first action potential voltage applied to the first electrode receptacle via the first electrode extension, and a second action potential voltage applied to the second electrode receptacle via the second electrode extension. In some embodiments, the third electrode extension connects a ground voltage of a subject from which the first and second action potential voltages originate to the EMG circuit as a reference voltage.

In one or more of the embodiments above, the circuit board is a base circuit board, and the EMG circuit includes a sibling circuit board that is removably mounted to the base circuit board in a stacked configuration such that the circuit boards are parallel, face each other, are spaced apart from each other, and are electrically connected.

In one or more of the embodiments above, the sibling circuit board lies within a second plane that is parallel to the first plane when it is mounted to the base circuit board, and the sibling circuit board comprises a third electrode receptacle sized to receive a third electrode extension. The third electrode receptacle includes an inlet having a centerline that extends through the third electrode receptacle in a direction parallel to the second plane. The third electrode extension may include a Tip Sleeve (TS) connector or a Tip Ring Sleeve (TRS) connector that connects the two action potential voltages to the difference circuit. In some such embodiments, the third electrode extension also connects a ground voltage of a subject from which the action potential voltages originate to the EMG circuit as a reference voltage.

In one or more of the embodiments above, the circuit board has a length defined along a major axis and a width defined along a minor axis arranged perpendicular to the major axis, the length is at least twice as long as the width, and the first and second openings are aligned along the major axis.

In one or more of the embodiments above, the sibling circuit board has a length defined along a major axis and a width defined along a minor axis arranged perpendicular to the major axis. In some such embodiments, the length of the sibling circuit board is less than or equal to the length of the base circuit board, and the width of the sibling circuit board is less than or equal to the width of the base circuit board.

In one or more of the embodiments above, the EMG circuit includes an energy storage device mounted and electrically connected to the sibling circuit board for powering the base circuit board and the sibling circuit board, wherein the energy storage device is within a profile defined by an outer perimeter of the sibling circuit board. In some such embodiments, the energy storage device comprises a battery, and the sibling circuit board comprises a battery clip to secure the battery to the sibling circuit board, and to electrically connect the battery to the sibling circuit board.

In one or more of the embodiments above, the EMG circuit includes a plurality of LEDs and an LED driver circuit mounted and electrically connected to the sibling circuit board, wherein the LED driver circuit is connected to the first EMG output signal, such that an amplitude of the first EMG output signal controls a quantity of the LEDs that are illuminated by the LED driver circuit.

In one or more of the embodiments above, the mounting is at least partially implemented via a plurality of mating electrical connectors, and the mating electrical connectors also electrically connect the sibling circuit board to the base circuit board. In some such embodiments, the plurality of mating electrical connectors comprise a plurality of first mating electrical connectors that extend outward from the base circuit board in a direction perpendicular to a face of the base circuit board, and a plurality of second mating electrical connectors that extend outward from the sibling circuit board in a direction perpendicular to a face of the sibling circuit board. One of the first and second plurality of mating electrical connectors are inserted into the other of the first and second plurality of mating electrical connectors to electrically connect and at least partially mount the sibling circuit board to the base circuit board.

In one or more of the embodiments above, the plurality of first mating electrical connectors include connectors on opposite ends of the face of the base circuit board, and the plurality of second mating electrical connectors includes connectors on opposite ends of the face of the sibling circuit board. In some such embodiments, In one or more of the embodiments above, a first one of the first mating electrical connectors and the second mating electrical connectors includes header pins, and a second one of the first mating electrical connectors and the second mating electrical connectors includes header connections into which the header pins are inserted.

In one or more of the embodiments above, the following items are mounted and electrically connected to the sibling circuit board: an analog-to-digital converter connected to the first EMG output signal, or another EMG output signal, from the base circuit board and configured to produce a corresponding digital EMG signal; and a wireless transmitter configured to wirelessly transmit a signal that is based on the digital EMG signal to the client device.

In one or more of the embodiments above, the difference circuit includes an instrumentation amplifier, the offset removal circuit includes a difference amplifier, the integration circuit includes an integration amplifier, and the rectification circuit includes either a full wave or a half wave rectification circuit.

According to another aspect of the present disclosure, an EMG circuit is disclosed that includes a base circuit board that has a length defined along a major axis and a width defined along a minor axis arranged perpendicular to the major axis, wherein the length is at least twice as wide as the width, and wherein the base circuit board lies within a plane. The circuit board includes first and second openings in the base circuit board that are spaced apart from each other on the circuit board and are aligned along the major axis. A first electrode receptacle is embedded in the first opening and is sized to receive a corresponding first electrode extension. The first electrode receptacle includes an inlet having a centerline that extends through the first electrode receptacle and is perpendicular to the plane. A second electrode receptacle is embedded in the second opening and is sized to receive a corresponding second electrode extension. The second electrode receptacle includes an inlet having a centerline that extends through the second electrode receptacle and is perpendicular to the plane. Circuit components that are mounted to the base circuit board are configured to amplify a difference between respective action potential voltages applied to the first and second electrode connectors to create an EMG signal, and to process the EMG to produce an EMG output signal for a client device. In some such embodiments, the first and second electrode receptacles are snap-in electrode receptacles.

According to another aspect of the present disclosure, a method is disclosed which is implemented by an EMG circuit. The EMG circuit receives action potential voltages from a plurality of electrodes, and creates an EMG signal based on a difference between action potential voltages of two of the plurality of electrodes. The creating of the EMG signal introduces a voltage offset, not already present in the action potential voltages, that centers the EMG signal about a non-zero voltage. The EMG circuit rectifies the EMG signal about the non-zero voltage to create a rectified EMG signal, and removes the voltage offset from the rectified EMG signal to create an adjusted EMG signal. The EMG circuit integrates the adjusted EMG signal to produce a first EMG output signal for a client device.

In one or more embodiments of the method, a power supply that powers the EMG circuit provides a voltage Vs to the EMG circuit, and the non-zero voltage about which the EMG signal is rectified is Vs/2.

In the same or other embodiments, the method also includes providing the EMG signal, prior to rectification, as a second EMG output signal to the same or another client device.

In one or more of the embodiments above, the voltage offset that is introduced into the action potential voltages is a first voltage offset, the action potential voltages include a second voltage offset prior to the creating of the EMG signal, and the method includes filtering the EMG signal to remove the second voltage offset from the EMG signal prior to the rectifying.

In one or more of the embodiments above, the method includes adjusting a luminance of an LED that is part of the EMG circuit based on an amplitude of the first EMG output signal, such that larger amplitudes output a higher luminance, and lower amplitudes output a lower luminance.

In one or more of the embodiments above, the EMG circuit comprises a circuit board and the two electrodes whose voltage difference is amplified include first and second electrodes. In such embodiments, the method includes connecting the first electrode to the circuit board by inserting a first electrode extension that is part of the first electrode into a first electrode receptacle in a snap-in connection, wherein the first electrode receptacle is embedded in a first opening of the circuit board. The method also includes connecting the second electrode to the circuit board by inserting a second electrode extension that is part of the second electrode into a different, second electrode receptacle in another snap-in connection, wherein the second electrode receptacle is embedded in a second opening of the circuit board. The first and second openings are spaced apart from each other on the circuit board and are aligned along a major axis of the circuit board.

In one or more of the embodiments above, the circuit board lies within a plane, the first electrode extension is inserted into the first electrode receptacle along a first axis that is perpendicular to the plane, and the second electrode extension is inserted into the second electrode receptacle along a different, second axis that is also perpendicular to the plane. In some such embodiments, the method includes connecting a third electrode to the circuit board by inserting a third electrode extension, which is connected to the third electrode, into a third electrode receptacle on the circuit board along a third axis that is parallel to the plane. The third electrode connects a ground voltage of a subject from which the action potential voltages originate to the EMG circuit as a reference voltage.

In one or more of the embodiments above, the circuit board is a base circuit board, and the method includes mounting a sibling circuit board to the base circuit board in a stacked configuration such that the circuit boards are parallel, face each other, and are spaced apart from each other, wherein the mounting comprises electrically connecting the sibling circuit board to the base circuit board.

In one or more of the embodiments above, mounting the sibling circuit board to the base circuit board includes aligning the base and sibling circuit boards such that the circuit boards face each other, and such that a first plurality of mating electrical connectors that extend outwardly in a perpendicular direction away from the base circuit board and a second plurality of the mating electrical connectors that extend outwardly in a perpendicular direction away from the sibling circuit board extend towards each other. The mounting also includes inserting one of the first and second plurality of mating electrical connectors into the other of the first and second plurality of mating electrical connectors to electrically connect and at least partially mount the sibling circuit board to the base circuit board. In some embodiments, a first one of the first and second plurality of mating electrical connectors comprises header pins, and a second one of the first and second plurality of mating electrical connectors comprises header connections sized for insertion of the header pins.

In one or more of the embodiments above, the method includes mounting and electrically connecting an energy storage device to the sibling circuit board, and powering the base circuit board and the sibling circuit board from the energy storage device.

In one or more of the embodiments above, a plurality of LEDs and an LED driver circuit are mounted and electrically connected to the sibling circuit board, and the method includes applying the first EMG output signal to the LED driver circuit, such that an amplitude of the first EMG output signal controls a quantity of the LEDs that are illuminated by the LED driver circuit.

In one or more of the embodiments above, the method includes passing the first EMG output signal, or another EMG output signal of the EMG circuit, through an analog-to-digital converter to create a digital EMG signal; and wirelessly transmitting a signal based on the digital EMG signal to a client device.

In one or more of the embodiments above, the EMG circuit comprises a base circuit board that performs at least some of the receiving, creating, rectifying, removing, and integrating; and the two electrodes whose voltage difference is amplified include first and second electrodes. In some such embodiments, the method includes mounting a sibling circuit board to the base circuit board in a stacked configuration such that the circuit boards are parallel, face each other, and are spaced apart from each other, the mounting at least partially implemented via a plurality of mating connectors, wherein the sibling circuit board lies in a plane. The mounting includes electrically connecting the sibling circuit board to the base circuit board via the mating connectors, and inserting an electrode extension into an electrode receptacle on the sibling circuit board in a direction parallel to the plane, wherein the electrode extension comprises a Tip Sleeve (TS) connector or a Tip Ring Sleeve (TRS) connector that connects the first and second electrodes to the EMG circuit.

Of course, the present invention is not limited to the above features and advantages. Indeed, those skilled in the art will recognize additional features and advantages upon reading the following detailed description, and upon viewing the accompanying drawings.

BRIEF DESCRIPTION OF THE DRAWINGS

For convenience, similar reference numerals are used throughout the Figures to indicate similar elements.

DETAILED DESCRIPTION

The present disclosure describes an EMG circuit for creating an EMG output signal based on action potential voltages. These action potential voltages may be measured from a human subject, for example. In one or more embodiments, the EMG circuit includes a difference circuit, rectification circuit, offset removal circuit, and integration circuit. The difference circuit is configured to create an EMG signal based on a difference between two action potential voltages, wherein creation of the EMG signal introduces a voltage offset, not already present in the action potential voltages, that centers the EMG signal about a non-zero voltage. The rectification circuit is connected to the difference circuit and is configured to rectify the EMG signal about the non-zero voltage to create a rectified EMG signal. The offset removal circuit is connected to the rectification circuit and is configured to remove the voltage offset from the rectified EMG signal to create an adjusted EMG signal. The integration circuit is connected to the offset removal circuit and is configured to integrate the adjusted EMG signal to produce a first EMG output signal for a client device.

In some embodiments, the EMG circuit includes embedded snap-in electrode connectors for connecting to electrodes secured to a subject, such that the EMG circuit is wearable on the subject. In some embodiments, the EMG circuit is modular, and can be augmented by stacking additional sibling circuit boards on a base circuit board, with those sibling circuit board adding additional features (e.g., an electronic display, wireless communication features, alternate electrode connection features, etc.).

Figure 1:
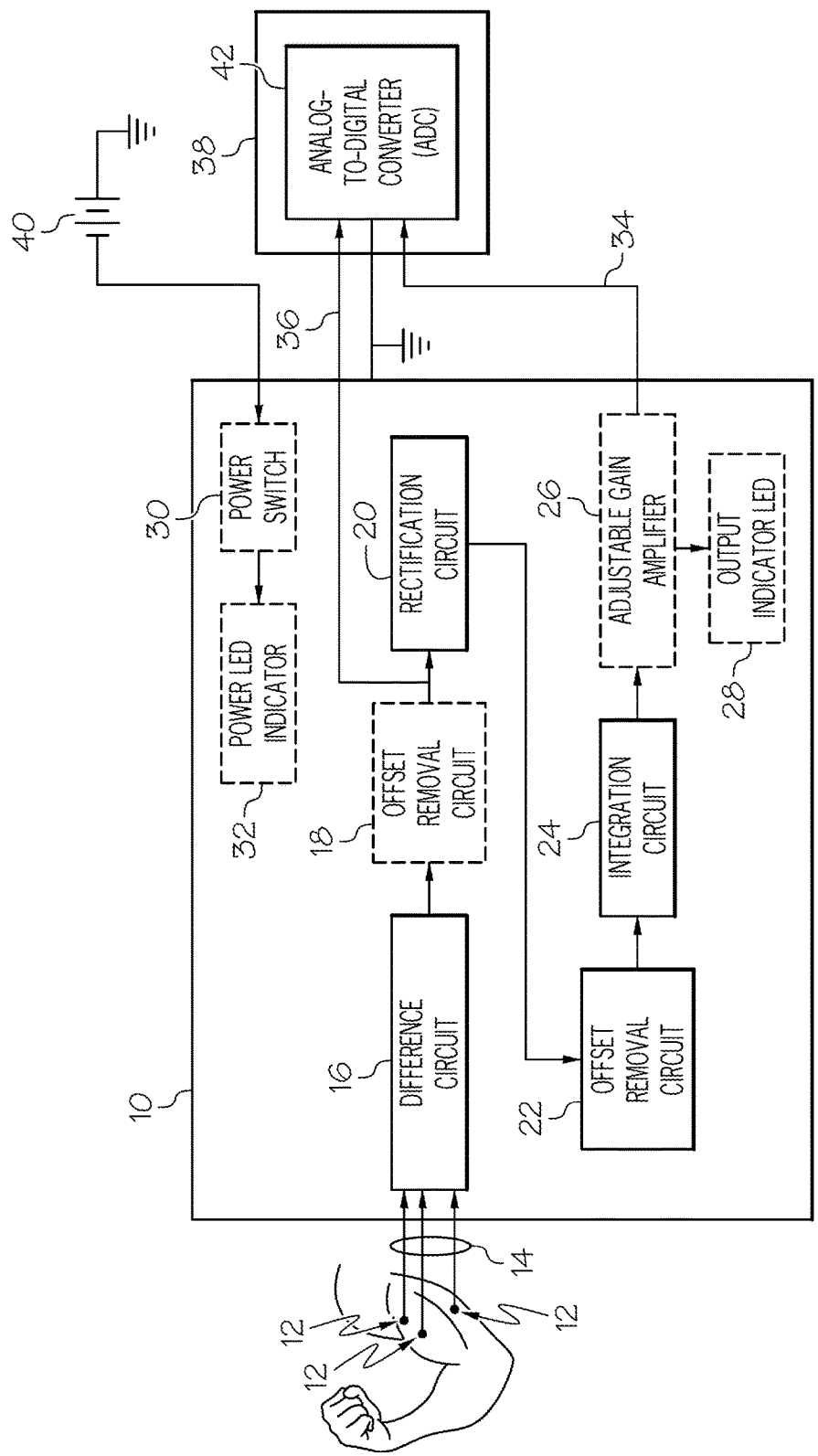
FIG. 1 schematically illustrates an example EMG circuit.

FIG. 1 schematically illustrates an example EMG circuit 10 that is electrically connected to electrodes 12 that are secured to a subject. The electrodes provide action potential voltages 14 to the EMG circuit 10. A difference circuit 16 is configured to create an EMG signal based on a difference between two of the action potential voltages 14. Creation of the EMG signal introduces a voltage offset, not already present in the action potential voltages, that centers the EMG signal about a non-zero voltage. This voltage offset will be called an "introduced voltage offset" herein because it is intentionally introduced by the EMG circuit 10. In one or more embodiments, the non-zero voltage about which the EMG signal is centered is Vs/2, where Vs is a voltage of a power supply of the EMG circuit 10. In some such embodiments, Vs/2 may serve as a virtual ground.

A rectification circuit 20 is connected to the difference circuit 12 (via the offset removal circuit 18 which is discussed in more detail below). The rectification circuit 20 is configured to rectify the EMG signal about the non-zero voltage to create a rectified EMG signal. An offset removal circuit 22 is connected to the rectification circuit 20 and is configured to remove the introduced voltage offset from the rectified EMG signal to create an adjusted EMG signal. An integration circuit 24 is connected to the offset removal circuit 22 and is configured to integrate the adjusted EMG signal to produce a first EMG output signal 34 for a client device 38. The first EMG output signal 34 can thus be an "EMG envelope". A number of client devices 38 could be used, such as computers, tablets, smartphones, development boards (e.g., ARDUINO, RASPBERRY PI, etc.), microcontrollers, etc.

Optionally, an adjustable gain amplifier 26 may be included, which is configured to adjust a gain of the EMG output signal 34. An output light-emitting diode (LED) indicator 28 may also be included, which is configured such that the EMG output signal 34 passes through the LED 28, and a luminance of the LED 28 varies based on an amplitude of the EMG output signal 34. Thus, the LED 28 may serve as an on-board muscle activity indicator that increases in brightness as a user flexes their muscles with a greater intensity.

The offset removal circuit 18 will now be discussed in greater detail. In one or more embodiments, the introduced voltage offset is a "first voltage offset," and the action potential voltages 14 include an additional second voltage offset (e.g., a DC offset) prior to the creation of the EMG signal by the difference circuit 16. This will be called an "inherent voltage offset" herein because it may be inherent to the action potential voltages 14, and is not introduced by the circuit 10. The inherent voltage offset and introduced voltage offset are distinct offsets. The EMG circuit 10 may comprise the offset removal circuit 18 as an additional offset removal circuit to remove the inherent voltage offset from the EMG signal prior to rectification by rectification circuit 20. The offset removal circuit 18 may be a high-pass filter, for example. This removal of the inherent offset can provide a symmetry of the EMG signal about its centerline (e.g., Vs/2), which may otherwise be absent if the inherent voltage offset was not removed.

A power supply 40 (e.g., a battery or some other energy storage device, such as a large capacitor) powers the EMG circuit 10. The power supply 40 could be a standalone power supply (e.g., an AC adapter), could be part of the client device 38, or could be part of a sibling circuit board, for example. A power switch 30 may be connected between the power supply 40 and the EMG circuit 10, to control whether the EMG circuit 10 is in an ON state or an OFF state. A power indicator LED 32 may be connected to the power switch to indicate whether the EMG circuit 10 is in the ON or OFF state. Components 18, 26, 28, 30, and 32 are optional components, and may be omitted from the EMG circuit 10 in some embodiments.

In addition to providing the envelope output signal 34, the EMG circuit 10 may also provide an additional EMG signal, prior to the rectification by rectification circuit 20, as a second EMG output signal to the same or another client device 38. The second EMG output signal 36 may be a raw EMG data signal 36 which has not been integrated. The client device may include an analog-to-digital converter (ADC) to process one or more of the EMG output signals 34, 36. Although shown in FIG. 1, an analog-to-digital converter (ADC) 42 may or may not be included in the client device 38.

In one or more embodiments, the power supply 40 that powers the EMG circuit 10 provides a voltage Vs to the EMG circuit 10, and the non-zero voltage about which the rectification circuit 20 rectifies the EMG signal is Vs/2.

In one or more embodiments, the difference circuit 16 is an instrumentation amplifier, the offset removal circuit 22 is a difference amplifier, the integration circuit 20 is an integration amplifier, and the rectification circuit 20 is either a full wave or a half wave rectification circuit.

In one or more embodiments, by using the EMG circuit 10, a user is able to take advantage of an entire analog input range of a microcontroller or ADC 42 used by client device 38. By rectifying the EMG signal about a non-zero voltage (e.g., $V_{REF}$=Vs/2), the entire EMG signal can be placed into a positive voltage plane before rectification (otherwise a negative portion of the waveform may be lost during rectification). Then, with subsequent removal of the introduced voltage offset, the EMG signal may have a 0 volts reference voltage, so that the entire resolution of an ADC can be utilized. Otherwise, half of the voltage range of the ADC may be forsaken. Assume, for example, that an ADC has a 10-bit resolution (1024 voltage levels=$2^{10}$). If the introduced voltage offset was not removed, that voltage range may be cut in half, reducing the resolution to a 9-bit resolution (512 voltage levels=$2^9$), because the entire EMG signal range would be from Vs/2-Vs instead of 0-Vs.

Figure 2:
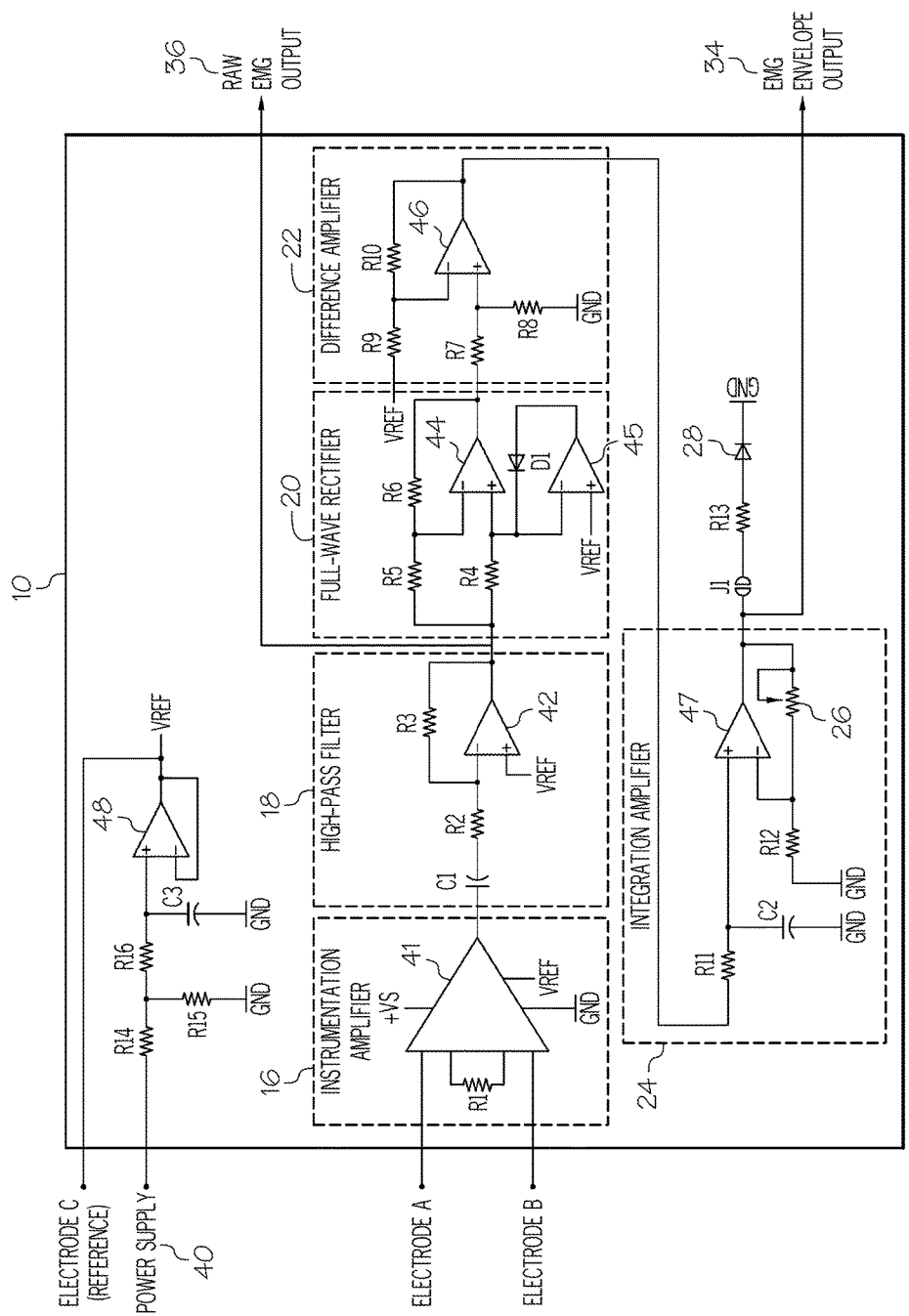
FIG. 2 illustrates an example embodiment of the EMG circuit of FIG. 1.

FIG. 2 illustrates an example embodiment of the EMG circuit 10 of FIG. 1. In the example of FIG. 2, the difference circuit 16 is an instrumentation amplifier that creates an EMG signal based on a difference between two action potential voltages. The two action potential voltages come from electrodes A and B, respectively. The EMG signal created by the instrumentation amplifier introduces "introduced voltage offset" that centers the EMG signal about a non-zero voltage. In one example, the non-zero voltage is Vs/2, where Vs is a voltage of power supply 40. The instrumentation amplifier includes operational amplifier (op-amp) 41, and resistor R1. Resistor R1 controls the gain of the instrumentation amplifier.

In the example of FIG. 2, the offset removal circuit 18 which removes the inherent voltage offset is a high-pass filter that includes op-amp 42, resistors R2 and R3, and capacitor C1.

In the example of FIG. 2, the rectification circuit 20 is a full-wave rectifier that takes the portion of the EMG signal that dips below the non-zero voltage about which the EMG signal is centered (e.g., Vs/2) and inverts that portion. The full-wave rectifier includes op-amps 44 and 45; resistors R4, R5, and R6; and diode D1.

In the example of FIG. 2, the offset removal circuit 22 which removes the introduced voltage offset is a difference amplifier that includes resistors R7, R8, R9, and R10, and includes op-amp 46.

In the example of FIG. 2, the integration circuit 24 is an integration amplifier that includes resistors R11 and R12, capacitor C2, and op-amp 47. The integration amplifier may also act as an adjustable gain amplifier by including potentiometer 26.

Output indicator LED 28 is connected to the EMG envelope signal 34 via resistor R13. A jumper J1 may be used to disable the output indicator LED 28 if desired. Alternatively, a switch could be used in place of the jumper J1.

A third electrode "C" is connected to the EMG circuit 10 and provides a reference voltage of a subject to which electrode C is attached. This could be used, for example, to determine a ground signal of the subject to which electrode C is attached. Resistors R14 and R15 act as a voltage divider to lower a voltage Vs of the power supply 40 to Vs/2. Resistor R16, capacitor C3 act as a low-pass filter to remove AC voltage signals from Vs. Op-amp 48 acts as a buffer amplifier to prevent impedance loading and interference. An output of op-amp 48, which may be Vs/2, is connected to a voltage potential of a subject from which the first and second action potential voltages originate (via electrode "C") to form a reference voltage $V_{REF}$. This may be used to effectively synchronize the subject's body electrical potential to the electrical potential of the EMG circuit 10.

In one or more embodiments, the EMG circuit 10 comprises a circuit board 50 that supports one or more of the difference circuit 16, rectification circuit 20, offset removal circuit 22, and integration circuit 24.

In some such embodiments, electrodes can snap directly to the circuit board 50, getting rid of the need for cables, and simplifying the setup of the EMG circuit 10. Through the use of certain electrodes, such as standard stick-on EMG electrodes which a user sticks onto their skin or electrodes embedded into wearable fabric, for example, a user may wear the EMG circuit 10 (see FIGS. 4-5).

Figure 3A:
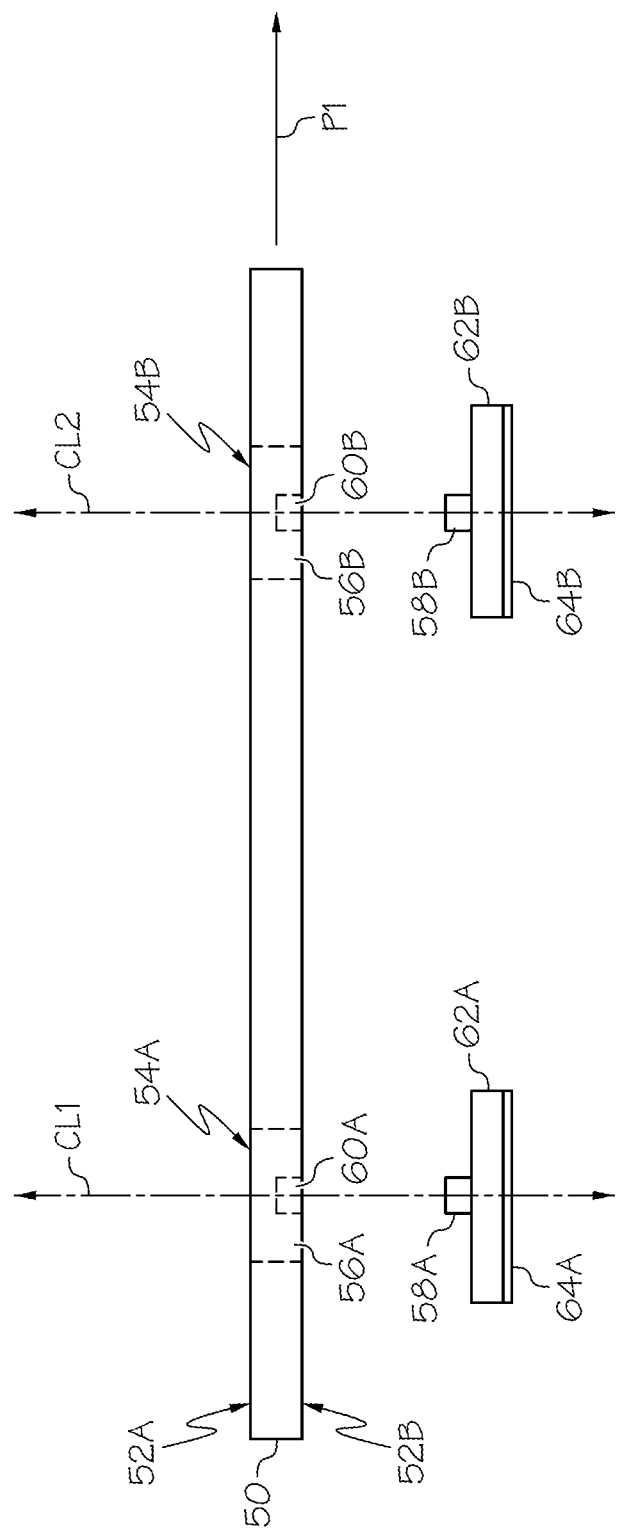
FIG. 3A schematically illustrates an example circuit board that may be used to implement the EMG circuit of FIG. 1.

FIG. 3A schematically illustrates an example circuit board 50 that may be used to implement the EMG circuit of FIG. 1. The circuit board 50 may include printed circuit board (PCB) connections to connect the various components of the EMG circuit 10. Although not shown in FIG. 3A, it is understood that these components could be affixed as surface mounted devices (SMDs). The circuit board 50 includes first and second openings 54A-B that are spaced apart from each other on the circuit board 50. The circuit board 50 lies within a first plane P1. The circuit board 50 includes a first side 52A and an opposing second side 52B. A first electrode receptacle 56A is sized to receive a corresponding first electrode extension 58A. The first electrode receptacle 56A has an inlet 60A having a centerline CL1 that extends through the first electrode receptacle 56A and is perpendicular to the first plane P1.

A second electrode receptacle 56B is sized to receive a corresponding second electrode extension 58B. The second electrode receptacle 56B includes an inlet 60B having a centerline CL2 that extends through the second electrode receptacle 56B and is perpendicular to the first plane P1. The first and second electrode receptacles 56A-B are snap-in electrode receptacles. Also, the first electrode receptacle 56A is embedded in the first opening 54A, and the second electrode receptacle 56B is embedded in the second opening 54B.

The first and second electrode receptacles 56A-B are snap-in electrode receptacles, whose respective inlets 60A-B form respective snap-in cavities. When electrode extension 58A is inserted into inlet 60A (or electrode extension 58B is inserted into inlet 60B), a positive tactile connection is formed.

The electrode extensions 58A, 58B may extend from respective electrodes 62A, 62B, each of which have a respective adhesive layer 64A, 64B for securing to a subject. In one or more embodiments, standard stick-on medical adhesive electrodes can be used. Of course, other snap-in electrodes could be used, such as those embedded in the fabric of clothing garments and/or dry electrode contacts, which may lack a gel layer or an adhesive layer 64.

Figure 3B:
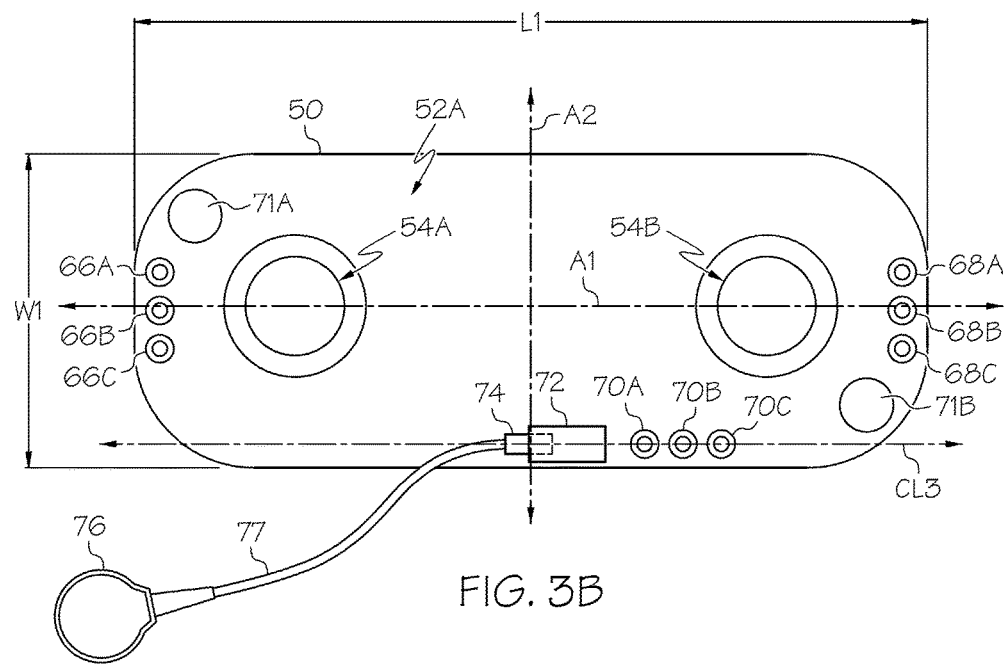
FIGS. 3B-3C illustrate opposing sides of the example circuit board according to one embodiment.
Figure 3C:
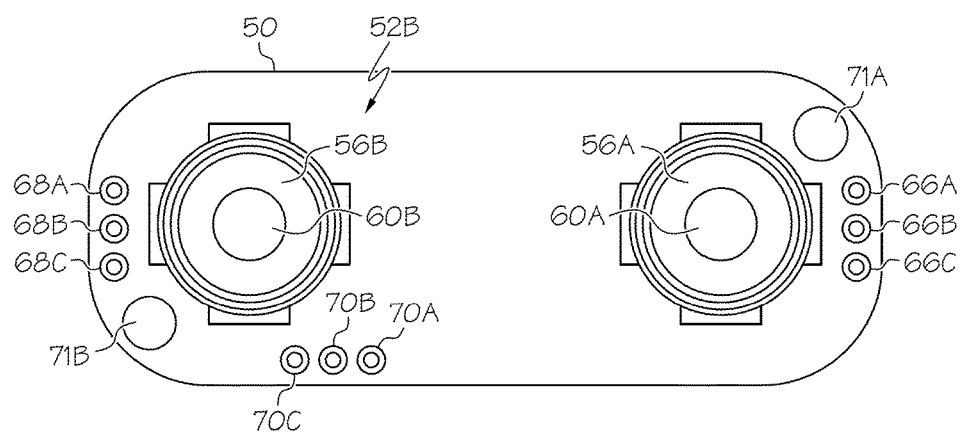

FIGS. 3B-C illustrate opposing sides 52A, 5B of the circuit board 50 according to one embodiment. As shown in these figures, the circuit board 50 may include a plurality of additional openings 66A-C, 68A-C, 70A-C, and 71A-B, which will be discussed in greater detail below. In the embodiment of FIG. 3B, the EMG circuit 10 includes a third electrode receptacle 72 that is mounted to the circuit board 50 and is sized to receive a third electrode extension 74. The third electrode receptacle 72 has a centerline CL3 that extends parallel to the first plane P1. In one or more embodiments, the third electrode extension 74 includes a spade terminal, and the third electrode receptacle 72 includes a spade terminal receptacle. Of course, it is understood that these are only example connectors, and that other types of connectors could be used. In the embodiment of FIG. 3B, the third electrode extension 74 connects to an additional snap-in electrode connector 76 via a lead wire 77.

In one or more embodiments, the two action potential voltages whose difference the difference circuit 16 uses to create an EMG signal comprise a first action potential voltage applied to the first electrode receptacle 60A via the first electrode extension 58A, and a second action potential voltage applied to the second electrode receptacle 60B via the second electrode extension 58B. In some embodiments, the third electrode extension 74 connects a ground voltage potential of a subject from which the first and second action potential voltages originate to the EMG circuit 10 to form a reference voltage (e.g., $V_{REF}$ in FIG. 2) common to both the body and EMG circuit 10.

Figure 4:
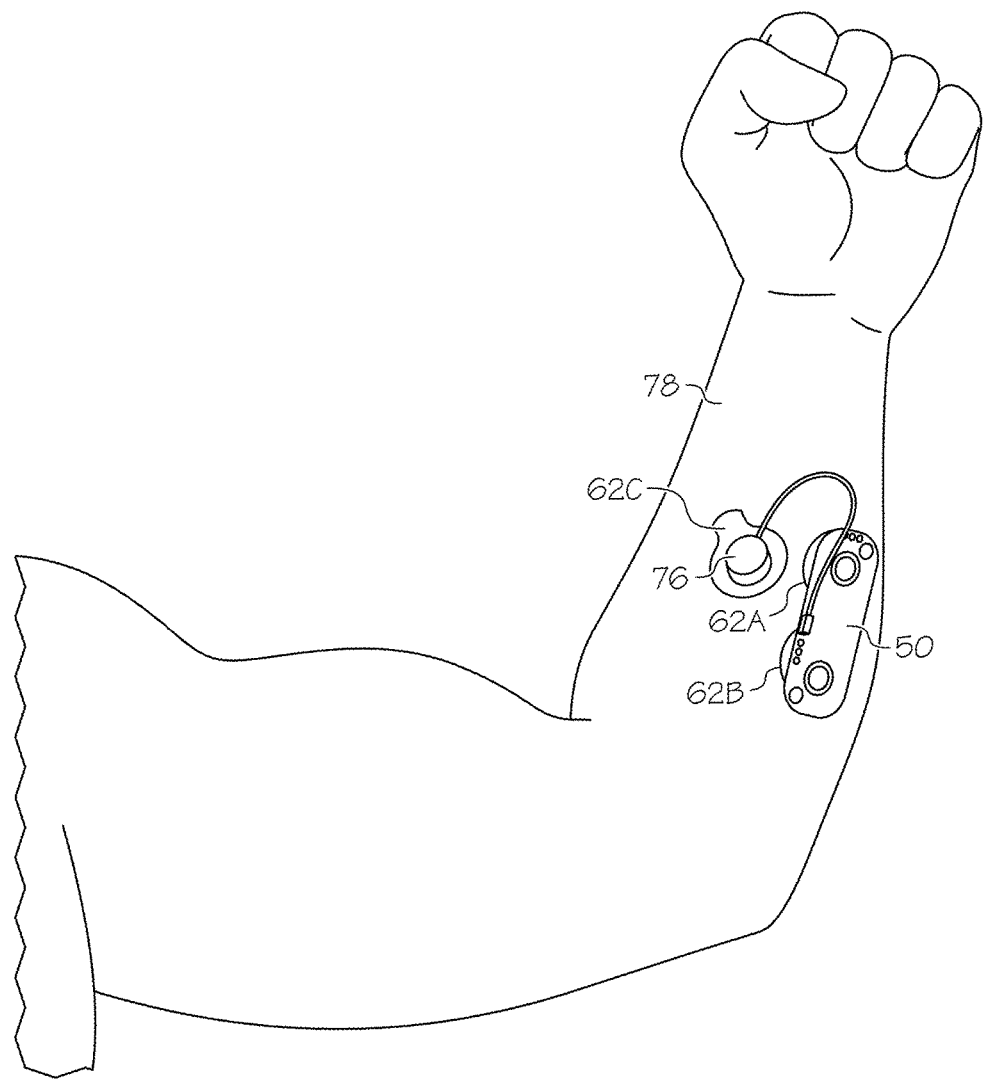
FIGS. 4-5 illustrates example ways in which the EMG circuit board of FIGS. 3A-C may be affixed to a subject.
Figure 5:
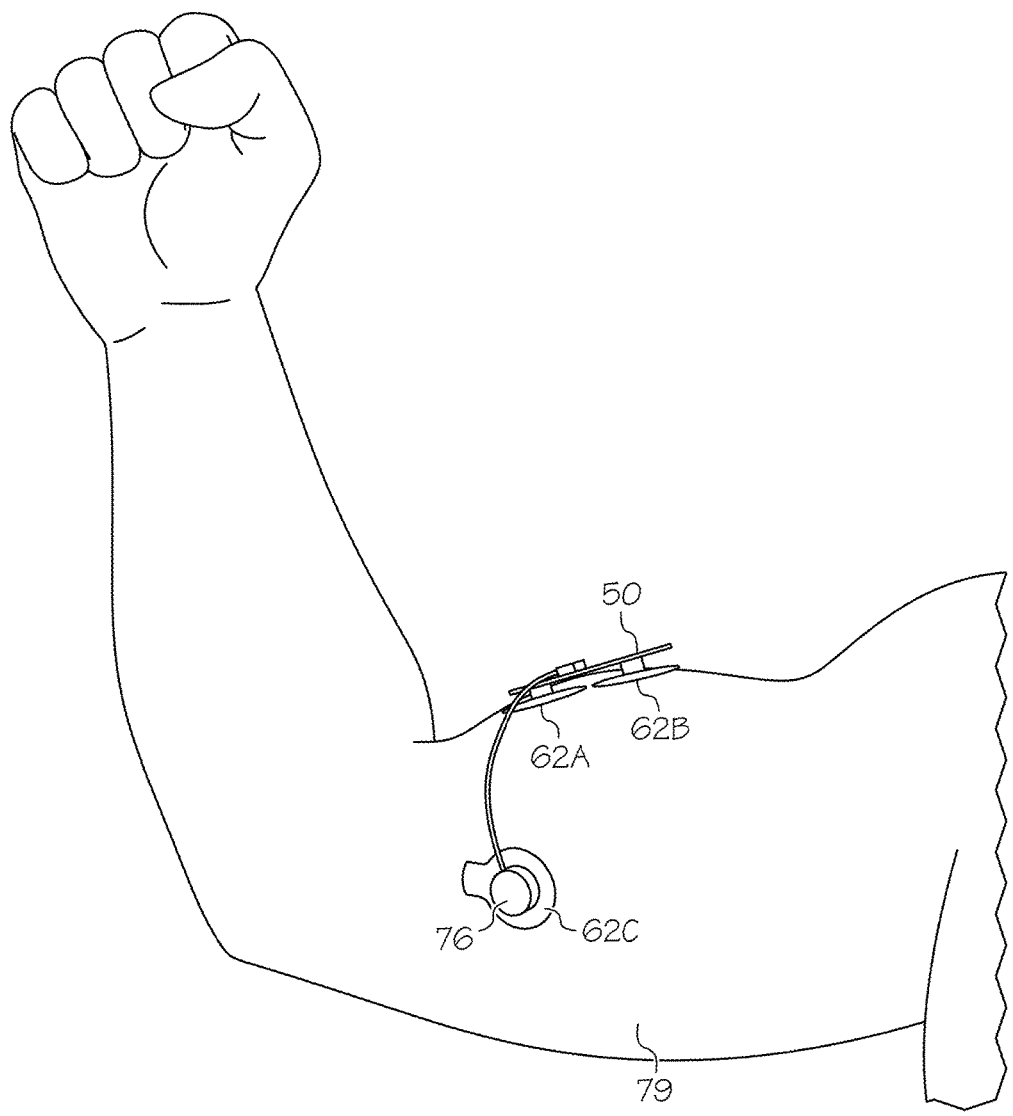

FIGS. 4-5 illustrates example ways in which the EMG circuit 10 of FIG. 1 may be affixed to a subject. In the embodiment of FIG. 4, the electrodes 62A-C are affixed to the forearm 78 of a human subject and are snapped into electrode connectors of the circuit board 50. In particular, electrodes 62A-B are snapped in to the electrode receptacles 60A-B, respectively, and electrode 60C is snapped into electrode connector 76.

In the embodiment of FIG. 5, the electrodes 62A-C are affixed to the upper arm 79 of a human subject and are snapped into electrode connectors of the circuit board 50. In particular, electrodes 62A-B are snapped in to the electrode receptacles 60A-B, respectively, and electrode 60C is snapped into electrode connector 76. Of course, the electrode locations shown in FIGS. 4-5 are only examples, and it is understood that other body locations and muscle groups could be used for obtaining action potential voltages.

Referring again to FIG. 3B, the circuit board 50 has a length L1 defined along a major axis A1 and a width W1 defined along a minor axis A2 that is arranged perpendicular to the major axis A1. In one or more embodiments, the length L1 is at least twice as long as the width W1. In the same or other embodiments, the first and second openings 54A, 54B are aligned along the major axis A1. In one or more embodiments, a distance between the respective centers of the openings 54A, 54B is approximately 30 millimeters. Of course, other spacing values could be used. The spacing could be varied to achieve a desired electrode positioning on a subject.

In one or more embodiments, the circuit board 50 is a base circuit board, and the EMG circuit 10 further comprises a sibling circuit board 80 that is removably mounted to the base circuit board 50 in a stacked configuration such that the circuit boards 50, 80 are parallel, face each other, are spaced apart from each other, and are electrically connected. As will be described below in greater detail, the sibling circuit board 80 may be used to piggyback on to the base circuit board 50, to augment the functionality of the base circuit board 50 in a modular fashion. The sibling circuit board 80 could be used to provide a power supply, to provide wireless capabilities, to connect one or more electrodes to the base circuit board 50, and/or to provide an electronic display, for example.

Figure 6A:
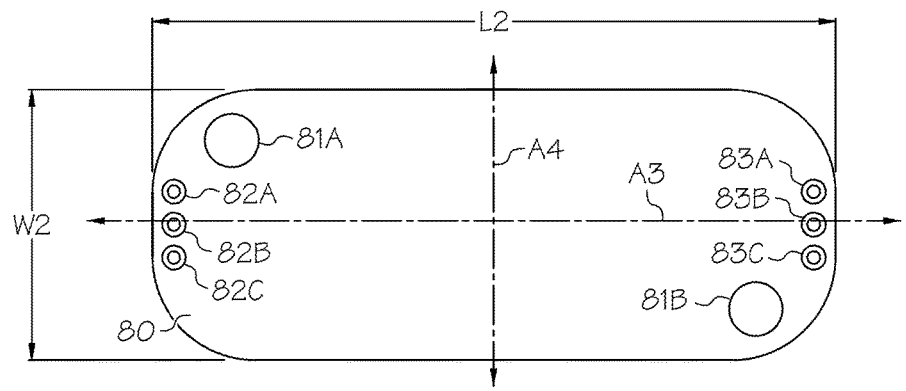
FIG. 6A illustrates an example sibling circuit board.

FIG. 6A illustrates an example sibling circuit board 80 that may be mounted and electrically connected to the base circuit board 50. The sibling circuit board 80 has a length L2 defined along a major axis A3 and a width W2 defined along a minor axis A4 arranged perpendicular to the major axis A3. In one or more embodiments the length L2 of the sibling circuit board 80 is less than or equal to the length L1 of the base circuit board 50, and the width W2 of the sibling circuit board 80 is less than or equal to the width W1 of the base circuit board 50.

The sibling circuit board 80 includes openings 81A-B, 82A-C, and 83A-C. Openings 81A-B may be aligned with openings 71A-B in base circuit board 50 for mounting the sibling circuit board 80 to the base circuit board 50. For example, a fastener could be inserted through each of the openings 71A, 81A (and similarly through openings 71B, 81B) to mount the circuit boards 50, 80 together.

Figure 6B:
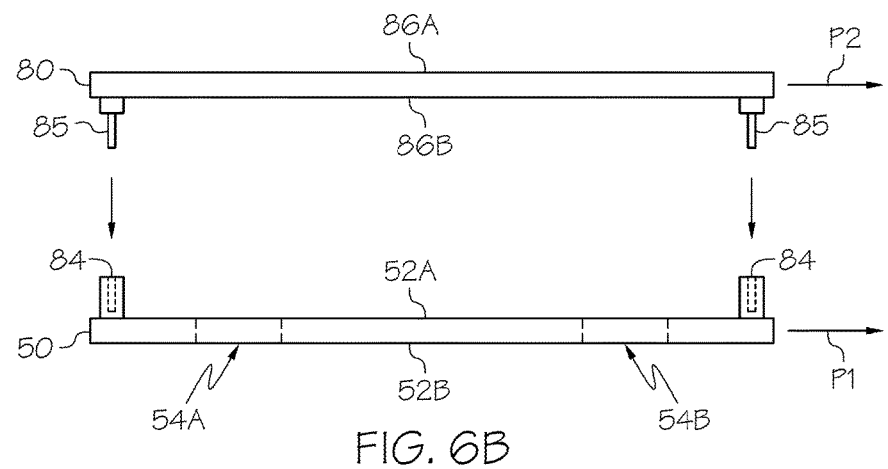
FIGS. 6B-C illustrate how the sibling circuit board of FIG. 6A may be mounted and electrically connected to the circuit board of FIG. 3A.
Figure 6C:
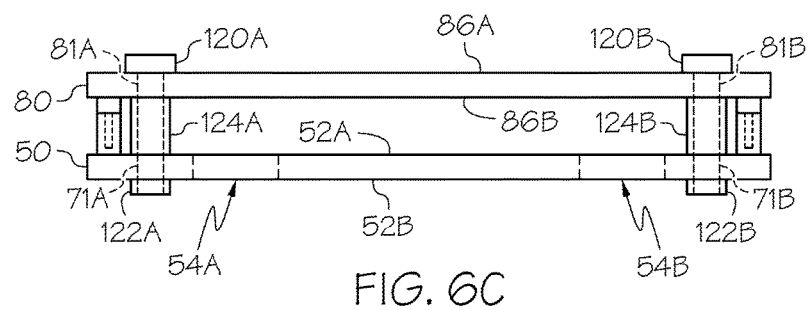

FIGS. 6B-C illustrate how the sibling circuit board 80 may be mounted and electrically connected to the base circuit board 50. In the example of FIGS. 6B-C, the mounting is at least partially implemented via a plurality of mating electrical connectors 84, 85 wherein the mating electrical connectors 84, 85 also electrically connect the sibling circuit board 80 to the base circuit board 50. When mounted to the base circuit board 50, the sibling circuit board lies within a second plane P2. In one or more embodiments, the second plane P2 is parallel to the first plane P1.

In one or more embodiments, the plurality of mating electrical connectors comprises a plurality of first mating electrical connectors 84 that extend outward from the base circuit board 50 in a direction perpendicular to a face of the base circuit board (i.e., perpendicular to the side 52A of the base circuit board 50), and a plurality of second mating electrical connectors 85 that extend outward from the sibling circuit board 80 in a direction perpendicular to a face of the sibling circuit board (i.e., perpendicular to the side 86B of the sibling circuit board 80). In such embodiments, one of the first and second plurality of mating electrical connectors 84, 85 are inserted into the other of the first and second plurality of mating electrical connectors 84, 85 to electrically connect and at least partially mount the sibling circuit board 80 to the base circuit board 50.

In one or more embodiments, the plurality of first mating electrical connectors 84 includes connectors on opposite ends of the face of the base circuit board 50 (i.e., opposite ends of side 52A of the base circuit board 50), and the plurality of second mating electrical connectors 85 includes connectors on opposite ends of the face of the sibling circuit board 80 (i.e., opposite ends of the side 86B of the sibling circuit board 80).

In one or more embodiments, a first one of the first electrical connectors and the second electrical connectors 84, 85 comprises header pins, and a second one of the first electrical connectors and the second electrical connectors 84, 85 comprises header connections into which the header pins are inserted. In the example embodiment of FIGS. 6A-B, it is the connectors 85 which comprise header pins that are inserted into the connectors 84 which comprise header connections into which the pins are inserted, however this could be switched such that the header pins are on the sibling board 80 instead of the base circuit board. In one or more embodiments, connectors 84 are secured and soldered to openings 66, 68 in the base circuit board 50, and connectors 85 are secured and soldered to openings 82, 83 in the sibling circuit board 80.

To further secure the sibling circuit board 80 to the base circuit board 50, fasteners such as bolts 120 may be used. As shown in FIG. 6C, a bolt 120A may be inserted into openings 81A and 71A, as well as through an optional sleeve 124A that can act as a spacer to maintain a desired distance between the circuit boards 50, 80. A nut 122A may be situated against the base circuit board 50 to secure to the bolt 120A. A bolt 120A inserted into openings 81B, 71B may be secured in the same fashion, using nut 122A and optionally also sleeve 124B. In some embodiments, the spacer sleeves 124 are omitted. In some embodiments, the nuts 122 may be omitted (e.g., if the openings 81, 71 are threaded). In some embodiments, no fastener is used, as the mounting provided by connectors 84, 85 may be sufficient.

Use of a fastener inserted into one or both of the openings could facilitate use of other types of connectors than the header pins 85 and header connections 84 shown in FIGS. 6B-C. For example, connectors could be used that abut each other instead of having a male-female connection, and the mounting feature offered by the header pins 85 and header connections 84 could be omitted.

Figure 7A:
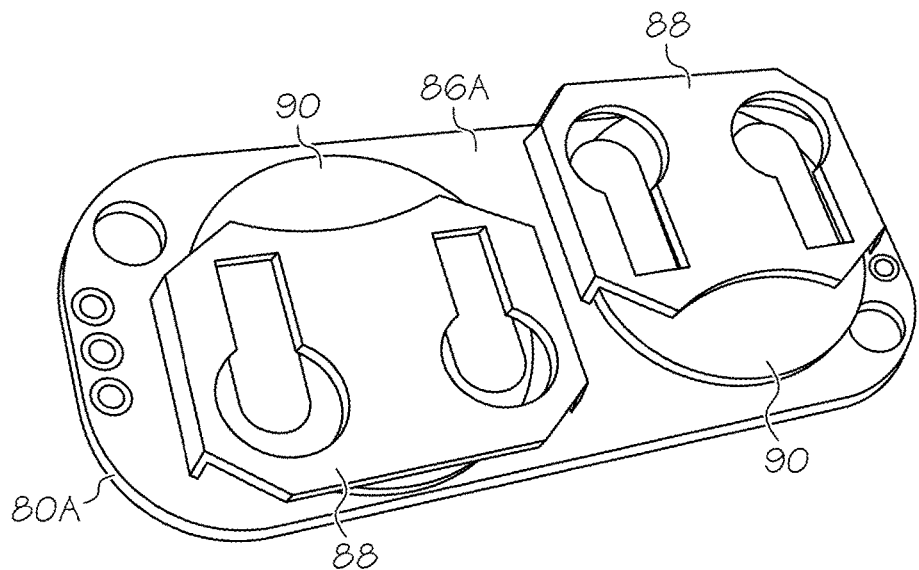
FIGS. 7A-7B illustrate opposing sides of an example sibling circuit board.
Figure 7B:
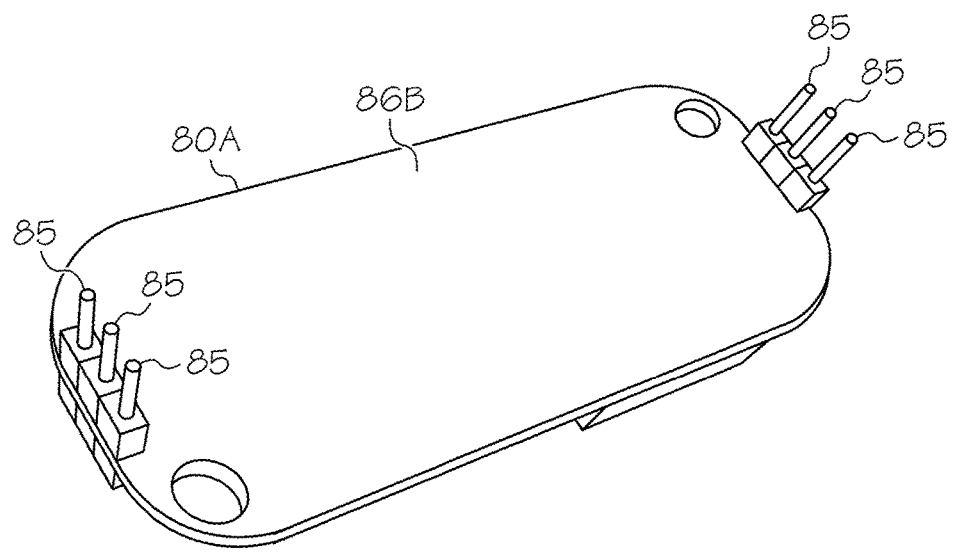

FIGS. 7A-7B illustrate opposing sides of an example sibling circuit board 80A that may be connected to the base circuit board 50 of FIGS. 3A-3B. FIG. 7A illustrate battery clips 88 that secure batteries 90 to the sibling circuit board 80, and electrically connect the batteries 90 to the sibling circuit board 90. Although multiple batteries 88 are shown, it is understood that in some embodiments a single battery 90 could be mounted and connected via a single battery clip 88.

Thus, in one or more embodiments, an energy storage device (e.g., battery 88) is mounted and electrically connected to the sibling circuit board 80 for powering the base circuit board 50 and the sibling circuit board 80, wherein the energy storage device is within a profile defined by an outer perimeter of the sibling circuit board 80. In some embodiments (e.g., that of FIG. 7A), the energy storage device comprises a battery 90, and the sibling circuit board 80 comprises a battery clip 88 to secure the battery 90 to the sibling circuit board 80, and to electrically connect the battery 90 to the sibling circuit board 80.

Figure 8A:
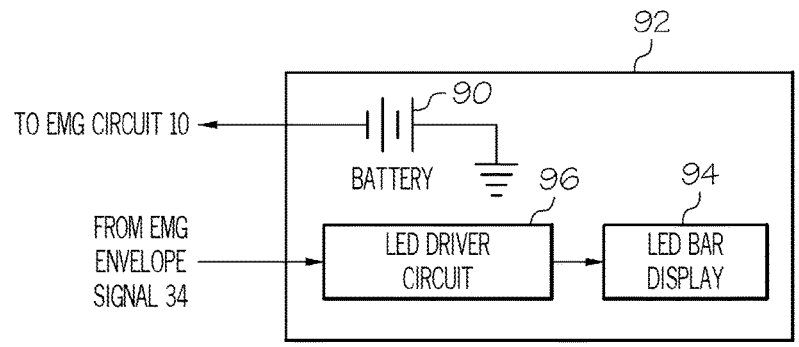
FIG. 8A schematically illustrates an example sibling circuit.
Figure 8B:
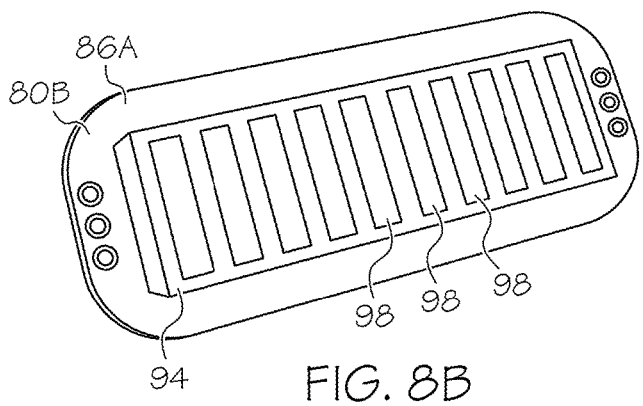
FIGS. 8B-C illustrate opposing sides of an example sibling circuit board that may be used to implement the circuit of FIG. 8A.
Figure 8C:
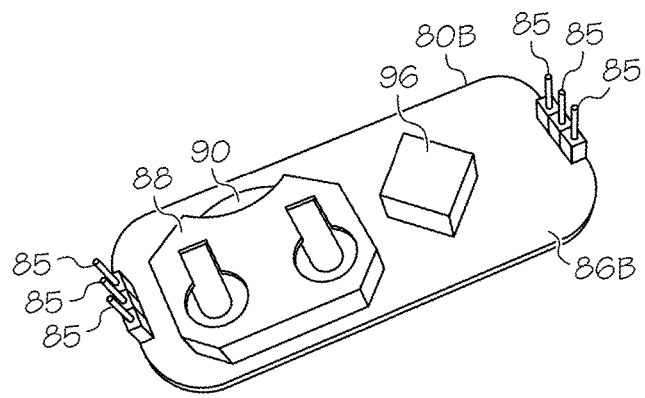

FIG. 8A schematically illustrates an example sibling circuit 92 that comprises an electronic display in the form of an LED bar display 94 that is connected to an LED driver circuit 96 (e.g., an analog LED driver circuit). FIGS. 8B-C illustrate opposing sides of an example sibling circuit board 80B that may be used to implement the circuit 92. The sibling circuit board 80B includes a first side 86A (see FIG. 8B) and an opposing second side (see FIG. 8C). In these figures, a plurality of LEDs (see LED bar display 94) and an LED driver circuit 96 are mounted and electrically connected to the sibling circuit board 80B. The LED driver circuit 96 may be connected to the first EMG output signal 34, such that an amplitude of the first EMG output signal 34 controls a quantity of the LEDs that are illuminated by the LED driver circuit 96. Thus, the harder a user flexes their muscles, they may control how many of the LEDs are illuminated in the LED bar display 94.

FIG. 8B illustrates a first side 86A of the sibling circuit board 80B, and FIG. 8C illustrates an opposite second side 86B of the sibling circuit board 80B. In the example of FIGS. 8B-C, the LED bar display 94 is situated on the first side 86A of the sibling circuit board 80A, and includes a plurality of transparent panels 98 through which the illumination of LEDs, which are beneath the panels 98 and are not shown in FIG. 8B, can be seen. In one example, each panel 98 has a corresponding LED beneath it. FIG. 8C illustrates how the LED driver circuit 96 can be situated on the opposing side 86B of the circuit board, and further illustrates how electrical header pins 85 can extend from the sibling circuit board 80B for mounting and electrically connecting the sibling circuit board 80B to the base circuit board 50.

Figure 9A:
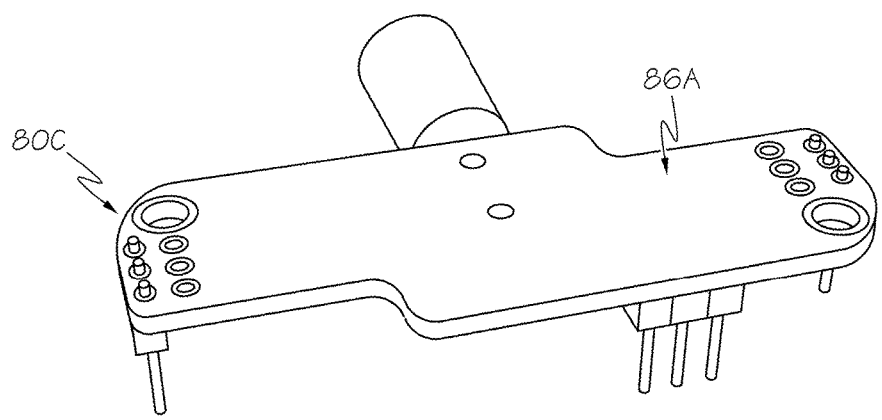
FIGS. 9A-9B illustrate opposing sides of another example sibling circuit board.
Figure 9B:
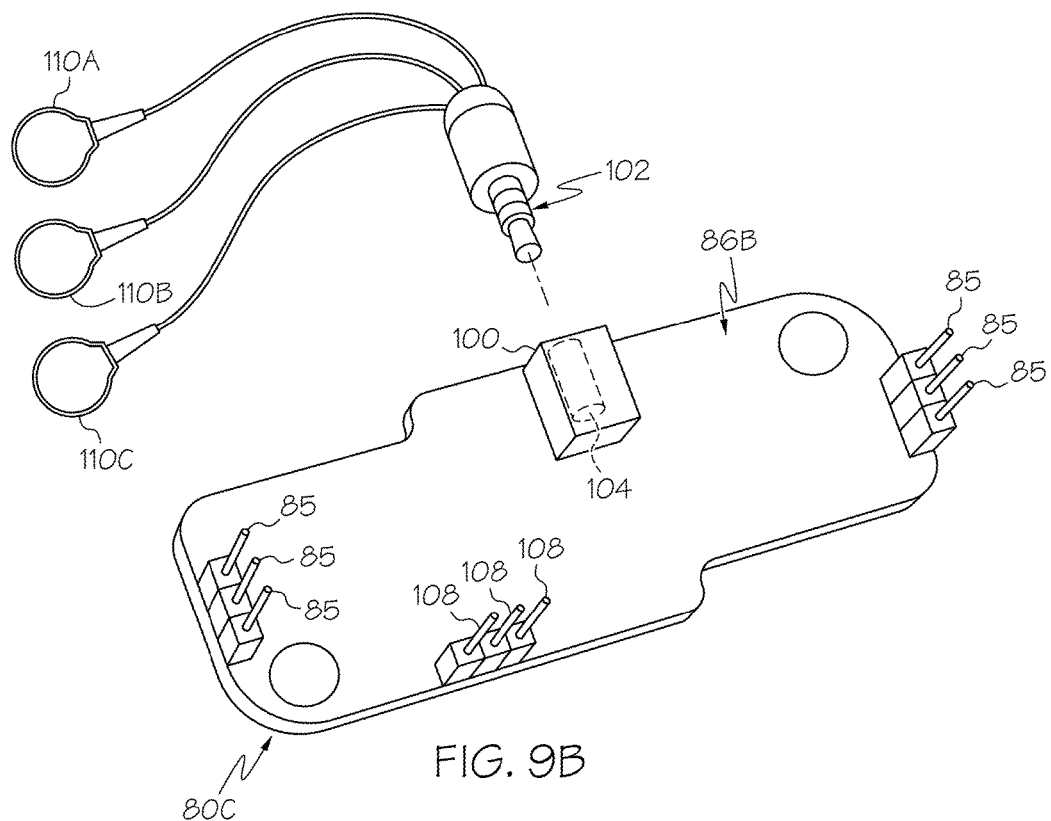

FIGS. 9A-9B illustrate opposing sides of another example sibling circuit board 80C that may be connected to the base circuit board 50 of FIGS. 3A-3B. The sibling circuit board 80C includes a first side 86A (see FIG. 9A) and an opposing second side (see FIG. 9B). The sibling circuit board 80C can be used to connect one or more electrodes to the base circuit board 50, e.g., as an alternative to using the electrode receptacles 56A-B and 72.

Figure 9C:
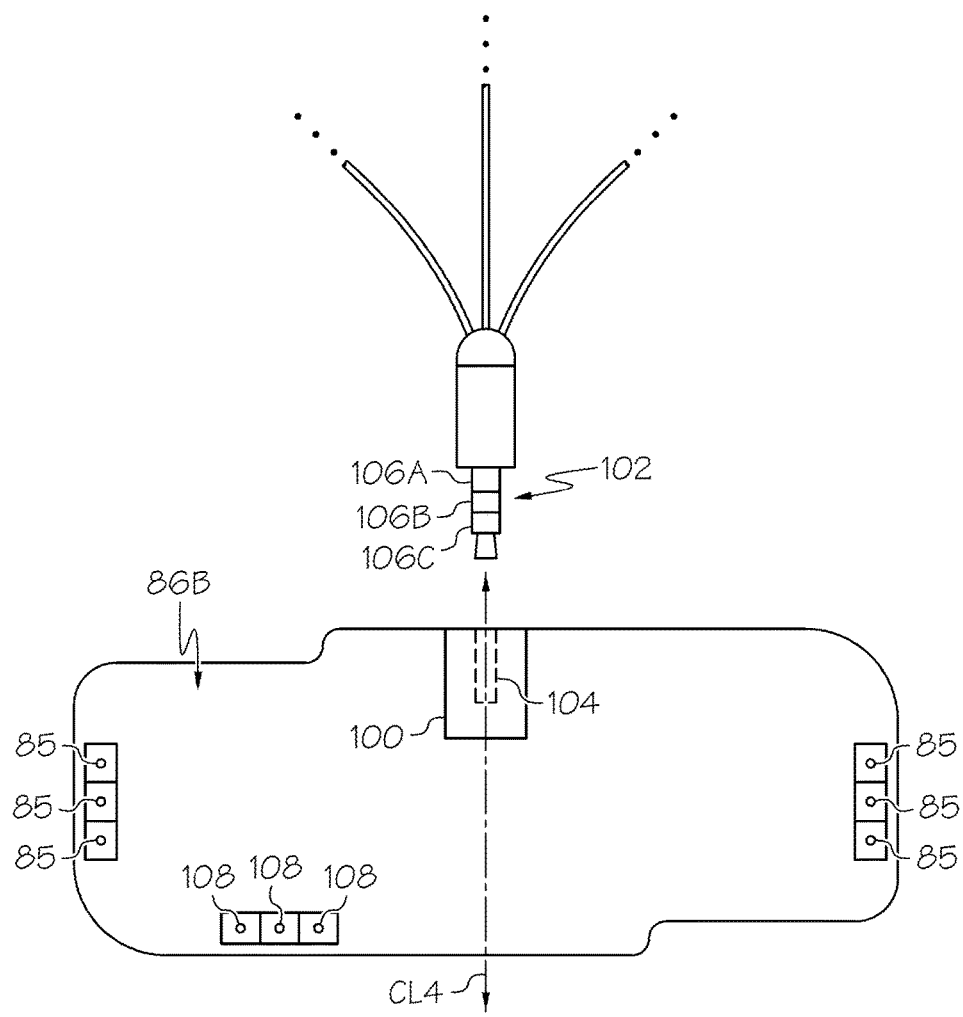
FIG. 9C illustrates another view of the sibling circuit board of FIGS. 9A-B.

FIG. 9C illustrates another view of side 86B of the sibling circuit board 80C. As in FIG. 6B, when the sibling circuit board 80C is mounted to the base circuit board 50, the sibling circuit board 80C lies within a second plane P2 that is parallel to the first plane P1. The sibling circuit board 80C comprises an electrode receptacle 100 that is sized to receive an electrode extension 102. The electrode receptacle 100 comprises an inlet 104 having a centerline CL4. In one or more embodiments, the centerline CL4 extends through the electrode receptacle 100 in a direction parallel to the second plane P2. The electrode extension 102 may comprise a Tip Sleeve (TS) connector or a Tip Ring Sleeve (TRS) connector that connects the two action potential voltages to the difference circuit, for example. This may take the form of a 3.5 mm audio jack, for example.

In the example of FIG. 9, the electrode extension 102 is a TRS connector that has three separate conductive regions 106A-C, each of which may be connected to a respective electrode. In such embodiments, the electrode extension 102 may connect a ground voltage of a subject from which the action potential voltages originate to the EMG circuit as a reference voltage. As discussed above, that reference voltage (i.e., a ground voltage potential of a subject from which the first and second action potential voltages originate) may be connected to the EMG circuit 10 to form a reference voltage $V_{REF}$ which is common to both the body and EMG circuit 10. In embodiments where a TS connector is used, two conductive regions 106 could be included instead of three, such that two electrodes would connect to the sibling circuit board 80C via the electrode connector 100. In one or more embodiments, the electrode extension 102 connects to three separate electrode connectors 110A-C, which are snap-in electrode connectors (see FIG. 9B)

The sibling circuit board 80C includes electrical connectors in the form of electrical header pins 85 that extend from the sibling circuit board 80B for mounting the sibling circuit board 80B to the base circuit board 50. The sibling circuit board 80C also includes additional connectors in the form of header pins 108 for connecting to header connections (not shown) mounted in openings 70A-C in the base circuit board 50. In one or more embodiments, the header pins 85 are only used for mounting purposes, and are either not conductive or are conductive but are not used by the sibling circuit board 80C for anything besides mounting. In the same or other embodiments, the header pins 108 are used for electrically connecting the sibling circuit board 80 to the base circuit board, by connecting conductive regions 106A-C to openings 70A-C of the base circuit board 50, in place of electrodes A-C.

Although the sibling circuit board 80C is shown with a profile that varies from the profile shown in FIG. 6A, it is understood that the same profile (e.g., that of FIG. 6A), or other profiles, could be used for any of the sibling circuit boards 80.

Figure 10A:
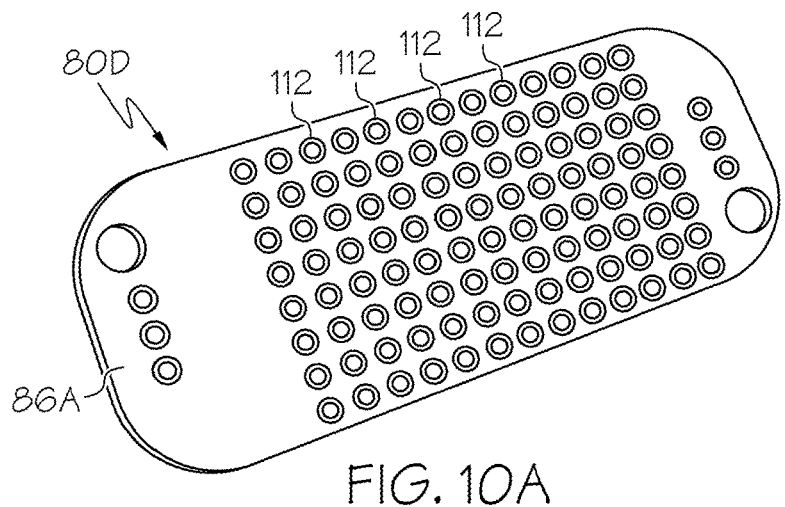
FIGS. 10A-10B illustrate opposing sides of another example sibling circuit board.
Figure 10B:
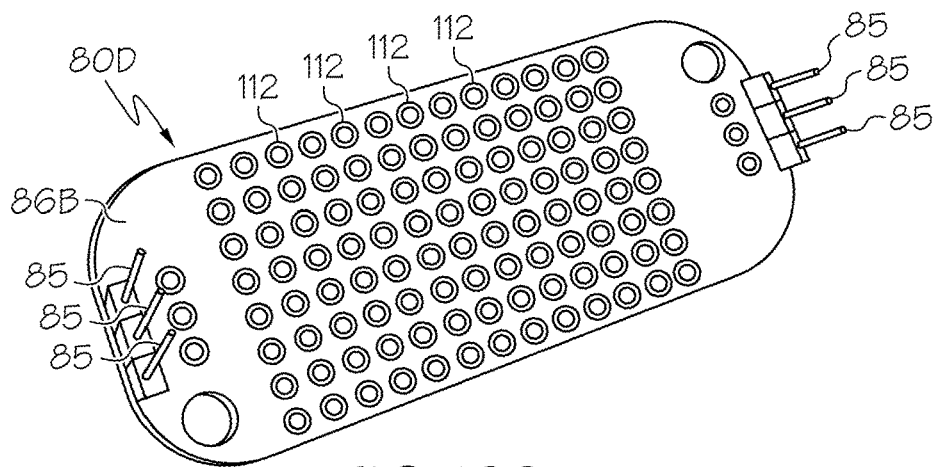

FIGS. 10A-B illustrates another example sibling circuit board 80D which includes a plurality of soldering holes into which components may be electrically connected, to serve as a blank template for users that wish to create their own sibling circuits. The sibling circuit board 80D includes a first side 86A and an opposite second side 86B, which may include header pins 85 for connecting to the base circuit board 50.

Figure 11:
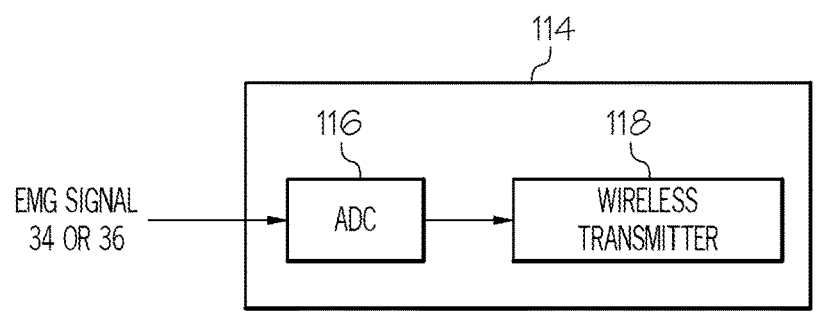
FIG. 11 schematically illustrates another example sibling circuit.

FIG. 11 illustrates a sibling circuit 14 that can be used to introduce wireless communication features to the EMG circuit 10. In the embodiment of FIG. 11, both an analog-to-digital converter (ADC) 116 and a wireless transmitter 118 are included. Both of these components could be mounted and electrically connected to a sibling circuit board 80. The ADC 116 is connected to the first EMG output signal 34, or another EMG output signal (e.g., raw EMG output 36), from the base circuit board 50 and is configured to produce a corresponding digital EMG signal. The wireless transmitter 118 is configured to wirelessly transmit a signal that is based on the digital EMG signal to a client device.

In one or more embodiments the wireless transmitter is configured according to one or more wireless standards, such as BLUETOOTH, a 802.11 standard, or one or more 3rd Generation Partnership Project (3GPP) standards such as GSM, WCDMA, or LTE. The wireless transmitter 118 may, in some embodiments, be a wireless transceiver that is also operable to receive wireless signals. This could be useful, e.g., for a BLUETOOTH pairing, or for receiving acknowledgement (ACK)/negative acknowledgement (NACK) signals from a client device 38.

As discussed above, the base circuit board 50 can be used to implement the EMG circuit 10 of FIG. 1. In other embodiments, the base circuit board 50 could be used to implement a different EMG circuit 10 that while still using the electrode connectors 56A-56B. Thus, in some embodiments an EMG circuit (whether the EMG circuit 10 or another EMG circuit) comprises a base circuit board 50 that has a length L1 defined along a major axis A1 and a width W1 defined along a minor axis A2 arranged perpendicular to the major axis A1, wherein the length L1 is at least twice as wide as the width W2, and wherein the base circuit board 50 lies within a plane P1 (see FIGS. 3A-B). The base circuit board 50 includes first and second openings 54A-B that are spaced apart from each other on the circuit board 50 and are aligned along the major axis A1. A first electrode receptacle 56A is embedded in the first opening 54A and is sized to receive a corresponding first electrode extension 58A. The first electrode receptacle 56A comprises an inlet 60A having a centerline CL1 that extends through the first electrode receptacle 56A and is perpendicular to the plane P1

A second snap-in electrode receptacle 56B is embedded in the second opening 54B and is sized to receive a corresponding second electrode extension 58B. The second electrode receptacle 56B comprises an inlet 60B having a centerline CL2 that extends through the second electrode receptacle 56B and is perpendicular to the plane P1. Circuit components are mounted to the base circuit board and are configured to amplify a difference between respective action potential voltages applied to the first and second electrode connectors 56A-B to create an EMG signal, and process the EMG to produce an EMG output signal for a client device (e.g., EMG output signal 34 or 36). The first and second electrode receptacles 56A-B may be snap-in electrode receptacles.

Figure 12:
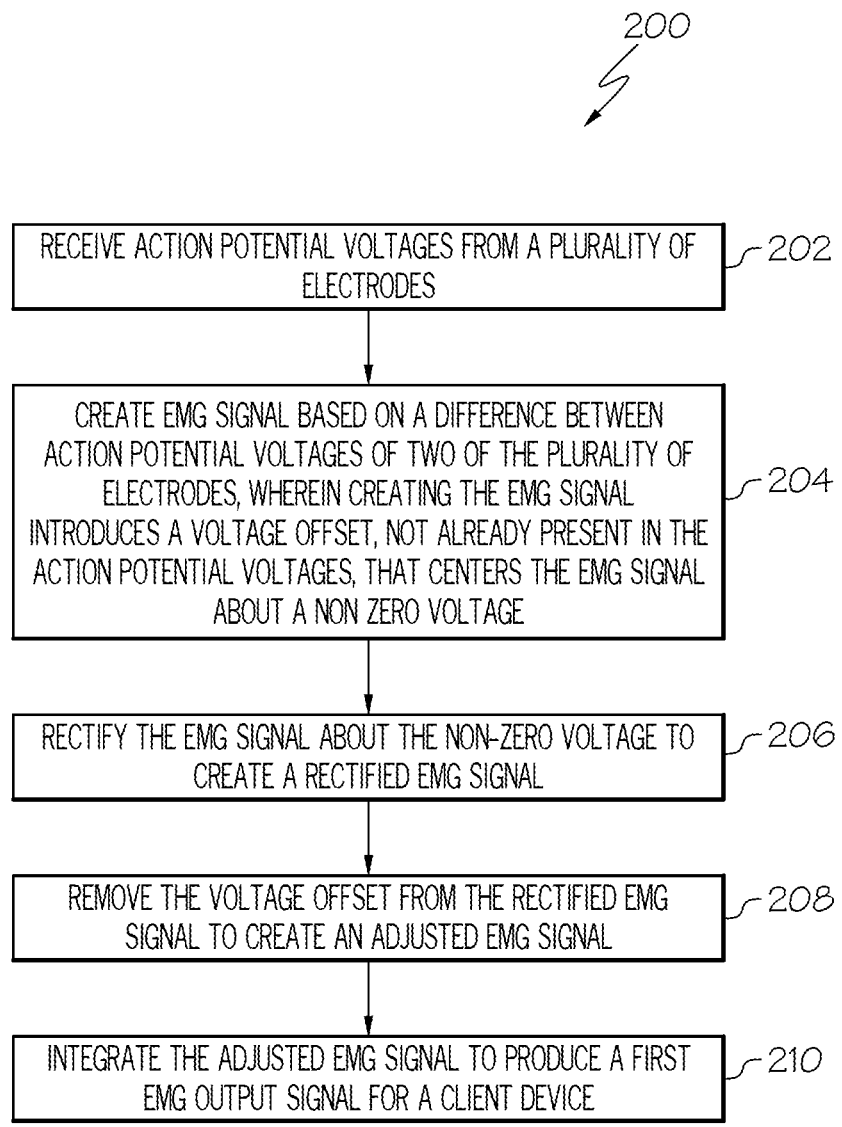
FIG. 12 is a flowchart of an example method that may be implemented by the EMG circuit of FIG. 1.

FIG. 12 illustrates a method 200 implemented by an electromyography (EMG) circuit 10. The EMG circuit 10 receives action potential voltages 14 from a plurality of electrodes (block 202), and creates an EMG signal based on a difference between action potential voltages of two of the plurality of electrodes (block 204). The creating of the EMG signal (block 204) introduces a voltage offset, not already present in the action potential voltages, that centers the EMG signal about a non-zero voltage (i.e., the "introduced voltage offset"). The EMG circuit rectifies the EMG signal about the non-zero voltage to create a rectified EMG signal (block 206), removes the voltage offset from the rectified EMG signal to create an adjusted EMG signal (block 208), and integrates the adjusted EMG signal to produce a first EMG output signal 34 for a client device 38 (block 210).

In one or more embodiments, a power supply 40 that powers the EMG circuit 10 provides a voltage Vs to the EMG circuit 10, and the non-zero voltage about which the EMG signal is rectified is Vs/2.

In one or more embodiments, the method 200 also includes providing the EMG signal, prior to the rectification (of block 206), as a second EMG output signal 346 to the same or another client device 38.

In one or more embodiments, the voltage offset that is introduced into the action potential voltages (the "introduced voltage offset") is a first voltage offset, and the action potential voltages 14 include a second voltage offset prior to the creating of the EMG signal (i.e., the "inherent voltage offset), and the method 200 further comprises filtering the EMG signal to remove the second voltage offset from the EMG signal prior to the rectifying of block 206. This filtering may be performed, e.g., by high-pass filter 18.

In one or more embodiments, the method 200 includes adjusting a luminance of an LED that is part of the EMG circuit based on an amplitude of the first EMG output signal, such that larger amplitudes output a higher luminance, and lower amplitudes output a lower luminance.

In one or more embodiments of the method 200, the EMG circuit 10 comprises a circuit board 50, and the two electrodes whose voltage difference is amplified include first and second electrodes 62A-B. In such embodiments, the method 200 further comprises connecting the first electrode 62A to the circuit board 50 by inserting a first electrode extension 58A that is part of the first electrode 62A into a first electrode receptacle 56A in a snap-in connection, wherein the first electrode receptacle is embedded in a 54A first opening of the circuit board 50. The method further comprises connecting the second electrode 62B to the circuit board 50 by inserting a second electrode extension 58B that is part of the second electrode 62B into a different, second electrode receptacle 56B in another snap-in connection, wherein the second electrode receptacle 56B is embedded in a second opening 54B of the circuit board 50. The first and second openings 54A-B are spaced apart from each other on the circuit board 50 and may be aligned along a major axis A1 of the circuit board 50.

In one or more embodiments of the method 200, the circuit board 50 lies within a plane P1, the first electrode extension 58A is inserted into the first electrode receptacle 56A along a first axis CL1 that is perpendicular to the plane P1, and the second electrode extension 58B is inserted into the first electrode receptacle 56B along a different, second axis CL2 that is also perpendicular to the plane P1. A third electrode 62C (see, e.g., FIGS. 4-5) is connected to the circuit board 50 by inserting a third electrode extension 74, connected to the third electrode 62C, into a third electrode receptacle 72 on the circuit board 50 along a third axis CL3 that is parallel to the plane P1. In some such embodiments, the third electrode 62C connects a ground voltage of a subject from which the action potential voltages originate to the EMG circuit 50 as a reference voltage (i.e., a ground voltage potential of a subject from which the first and second action potential voltages originate) which may be connected to the EMG circuit 10 to form a reference voltage (e.g., $V_{REF}$) common to both the subject and the circuit board 50.

In one or more embodiments, the circuit board is a base circuit board 50, and the method 200 further comprises mounting a sibling circuit board 80 to the base circuit board 50 in a stacked configuration such that the circuit boards 50, 80 are parallel, face each other, and are spaced apart from each other, wherein the mounting comprises electrically connecting the sibling circuit board 80 to the base circuit board 50.

In some embodiments, mounting the sibling circuit board 80 to the base circuit board 50 includes aligning the base and sibling circuit boards 50, 80 such that the circuit boards 50, 80 face each other, and such that a first plurality of mating electrical connectors 84 that extend outwardly in a perpendicular direction away from the base circuit board 50 and a second plurality of the mating electrical connectors 85 that extend outwardly in a perpendicular direction away from the sibling circuit board 80 extend towards each other. One of the first and second plurality of mating electrical connectors 84, 85 are inserted into the other of the first and second plurality of mating electrical connectors 84, 85 to electrically connect and at least partially mount the sibling circuit board 80 to the base circuit board 50.

In one or more embodiments, a first one of the first and second plurality of mating electrical connectors comprises header pins 85, and a second one of the first and second plurality of mating electrical connectors comprises header connections 84 sized for insertion of the header pins 85.

In one or more embodiments, the method 200 includes mounting and electrically connecting an energy storage device to the sibling circuit board 80, and powering the base circuit board 50 and the sibling circuit board 80 from the energy storage device. The energy storage device could include a battery in some embodiments. In some embodiments, an energy harvesting circuit (e.g., a solar cell or other energy harvesting device) could be used to charge the energy storage device, which could include a chargeable battery or capacitor, for example.

In one or more embodiments, a plurality of LEDs and an LED driver circuit 96 are mounted and electrically connected to the sibling circuit board 80, and the method 200 includes applying the first EMG output signal 34 to the LED driver circuit 96, such that an amplitude of the first EMG output signal 34 controls a quantity of the LEDs that are illuminated by the LED driver circuit (e.g., within LED bar display 94). This may be performed using the circuit 92 of FIG. 8A, for example, which uses LED driver circuit 96 to control how many LEDs in LED bar display 94 are illuminated.

In one or more embodiments (e.g., as shown in FIG. 11), the method 200 includes passing the first EMG output signal 34, or another EMG output signal of the EMG circuit 10 (e.g., signal 36), through an ADC 116 to create a digital EMG signal, and wirelessly transmitting a signal based on the digital EMG signal to a client device (e.g., via wireless transmitter 118).

In one or more embodiments of the method 200, the EMG circuit 10 includes a base circuit board 50 that performs at least some of the receiving (block 202), creating (block 204), rectifying (block 206), removing (block 208), and integrating (block 210), and the two electrodes whose voltage difference is amplified include first and second electrodes. In some such embodiments, the method 200 includes mounting a sibling circuit board 80 to the base circuit board in a stacked configuration such that the circuit boards 50, 80 are parallel, face each other, and are spaced apart from each other, the mating being at least partially implemented via a plurality of mating electrical connectors (e.g., 84, 85), wherein the sibling circuit board 80 lies in a plane P2. In some such embodiments, the mounting includes electrically connecting the sibling circuit board 80 to the base circuit board 50 via the mating connectors; and inserting an electrode extension into an electrode receptacle on the sibling circuit board in a direction parallel to the plane, wherein the electrode extension comprises a Tip Sleeve (TS) connector or a Tip Ring Sleeve (TRS) connector that connects the first and second electrodes to the EMG circuit 10 (see FIG. 9B-9C).

The embodiments discussed above can provide a number of advantages in some examples. Use of the snap-in electrode receptacles 56A-B, for example, may reduce setup time and cost by simplifying the process for affixing electrodes to a subject and to the EMG circuit 10. These snap-in connectors can also facilitate the wearing of the EMG circuit 10 by a subject (e.g., as shown in FIGS. 4-5). Also, the sibling circuit boards can be used to augment the functionality of the base circuit board, and may be highly customizable (e.g., using sibling circuit board 80D). Provision of the dual EMG output signals 34, 36, may be advantageous in certain environments as well.

As discussed above, the EMG circuit 10 can accommodate a variety of electrode configurations. The EMG circuit could be configured to accommodate either monopolar or bipolar EMG readings if desired. Monopolar EMG uses two electrodes, whereas bipolar EMG uses three electrodes. Either configuration could be accommodated by the EMG circuit 10. One example electrode configuration is shown in FIGS. 4-5, where two electrodes 62A-B are snapped in to the electrode receptacles 56A-B and a third electrode 62C is snapped into electrode connector 76 which connects to the EMG circuit via lead wire 77. Alternatively, two or three electrodes could be connected to the EMG circuit 10 via the sibling circuit board 80C of FIGS. 9A-C. Although surface electrodes have been discussed at length herein, it is understood that intramuscular electrodes could be used as well in some embodiments of the EMG circuit 10 if desired.

The EMG circuit 10 may be used in a variety of different applications. One example use is in exercise, as the EMG circuit 10 could be used to gauge how well a subject is exercising targeted muscle groups. As muscles fatigue, a magnitude of the EMG signal 34 would diminish. If a subject intended to exercise a group of muscles, but an EMG signal 34 of only one of those muscle groups was diminishing, the user could identify the muscle groups that were not being sufficiently utilized. If desired, this could be performed in an entirely analog fashion, without using software circuitry on a client device (e.g., by relying on the sibling circuit board 80B)

In other embodiments, the EMG circuit 10 could be used as a toy (e.g., if a person wished to apply an electrical signal based on muscle flexing—such as video game control or costume lighting control). For example, the EMG circuit 10 could be used to provide a hands-free way to trigger electrical and/or mechanical effects in a costume (e.g., by actuating a switch based on action potential voltages). The EMG circuit 10 could also be used in health rehabilitation embodiments (e.g., stroke rehabilitation and/or myoelectric controlled prosthetics).

The present disclosure may, of course, be carried out in other ways than those specifically set forth herein without departing from essential characteristics of the present disclosure. Moreover, the present embodiments are to be considered in all respects as illustrative and not restrictive, and all changes coming within the meaning and equivalency range of the appended claims are intended to be embraced therein. Thus, the foregoing description and the accompanying drawings represent non-limiting examples of the methods and apparatus taught herein. As such, the present disclosure is not limited by the foregoing description and accompanying drawings. Instead, the present disclosure is limited only by the following claims and their legal equivalents.

What is claimed is:

1. An electromyography (EMG) circuit comprising:
   a difference circuit comprising an operational amplifier coupled to two action potential voltages and configured to create an EMG signal based on a difference between the two action potential voltages, wherein creation of the EMG signal introduces a voltage offset, not already present in the action potential voltages, that centers the EMG signal about a non-zero voltage;
   a rectification circuit connected to the difference circuit and configured to rectify the EMG signal about the non-zero voltage to create a rectified EMG signal;
   an offset removal circuit connected to the rectification circuit and configured to remove the voltage offset from the rectified EMG signal to create an adjusted EMG signal; and
   an output circuit connected to the offset removal circuit and configured to produce a first EMG output signal for a client device based on the adjusted EMG signal, wherein the first EMG output signal is an EMG envelope signal.

2. The EMG circuit of claim 1, wherein a power supply that powers the EMG circuit provides a voltage Vs to the EMG circuit, and wherein the non-zero voltage about which the rectification circuit rectifies the EMG signal is Vs/2.

3. The EMG circuit of claim 1, comprising an output that provides the EMG signal, prior to the rectification, as a second EMG output signal to the same or another client device.

4. The EMG circuit of claim 1:
wherein the voltage offset introduced by the difference circuit is a first voltage offset;
wherein the action potential voltages include a second voltage offset prior to the creation of the EMG signal; and
wherein the EMG circuit comprises an additional offset removal circuit configured to remove the second voltage offset from the EMG signal prior to the rectification.

5. The EMG circuit of claim 4, wherein the additional offset removal circuit is a high-pass filter.

6. The EMG circuit of claim 1, comprising a light-emitting diode (LED) configured such that the first EMG output signal passes through the LED, and a luminance of the LED varies based on an amplitude of the first EMG output signal.

7. The EMG circuit of claim 1, wherein the EMG circuit comprises:
a circuit board that supports one or more of the difference circuit, rectification circuit, offset removal circuit, and output circuit, the circuit board having first and second openings that are spaced apart from each other on the circuit board, wherein the circuit board lies within a first plane;
a first electrode receptacle sized to receive a corresponding first electrode extension, the first electrode receptacle comprising an inlet having a centerline that extends through the first electrode receptacle and is perpendicular to the first plane;
a second electrode receptacle sized to receive a corresponding second electrode extension, the second electrode receptacle comprising an inlet having a centerline that extends through the second electrode receptacle and is perpendicular to the first plane;
wherein the first and second electrode receptacles are snap-in electrode receptacles; and
wherein the first electrode receptacle is embedded in the first opening, and the second electrode receptacle is embedded in the second opening.

8. The EMG circuit of claim 7:
wherein the EMG circuit comprises a third electrode receptacle that is mounted to the circuit board and is sized to receive a third electrode extension, wherein the third electrode receptacle has a central longitudinal axis that extends parallel to the first plane.

9. The EMG circuit of claim 8:
wherein the two action potential voltages comprise:
a first action potential voltage applied to the first electrode receptacle via the first electrode extension; and
a second action potential voltage applied to the second electrode receptacle via the second electrode extension; and
wherein the third electrode extension connects a ground voltage of a subject from which the first and second action potential voltages originate to the EMG circuit as a reference voltage.

10. The EMG circuit of claim 7, wherein the circuit board is a base circuit board, the EMG circuit comprising:
a sibling circuit board removably mounted to the base circuit board in a stacked configuration such that the circuit boards are parallel, face each other, are spaced apart from each other, and are electrically connected.

11. The EMG circuit of claim 10, wherein the circuit board has a length defined along a major axis and a width defined along a minor axis arranged perpendicular to the major axis, wherein the length is at least twice as long as the width, and wherein the first and second openings are aligned along the major axis.

12. The EMG circuit of claim 11, wherein the sibling circuit board has a length defined along a major axis and a width defined along a minor axis arranged perpendicular to the major axis, wherein the length of the sibling circuit board is less than or equal to the length of the base circuit board, and the width of the sibling circuit board is less than or equal to the width of the base circuit board.

13. The EMG circuit of claim 10, comprising an energy storage device mounted and electrically connected to the sibling circuit board for powering the base circuit board and the sibling circuit board, wherein the energy storage device is within a profile defined by an outer perimeter of the sibling circuit board.

14. The EMG circuit of claim 13, wherein the energy storage device comprises a battery, and the sibling circuit board comprises a battery clip to secure the battery to the sibling circuit board, and to electrically connect the battery to the sibling circuit board.

15. The EMG circuit of claim 10, comprising:
a plurality of light-emitting diodes (LEDs) and an LED driver circuit mounted and electrically connected to the sibling circuit board;
wherein the LED driver circuit is connected to the first EMG output signal, such that an amplitude of the first EMG output signal controls a quantity of the LEDs that are illuminated by the LED driver circuit.

16. The EMG circuit of claim 10:
wherein the mounting is at least partially implemented via a plurality of mating electrical connectors; and
wherein the mating electrical connectors also electrically connect the sibling circuit board to the base circuit board.

17. The EMG circuit of claim 16:
wherein the plurality of mating electrical connectors comprises:
a plurality of first mating electrical connectors that extend outward from the base circuit board in a direction perpendicular to a face of the base circuit board; and
a plurality of second mating electrical connectors that extend outward from the sibling circuit board in a direction perpendicular to a face of the sibling circuit board;
wherein one of the first and second plurality of mating electrical connectors are inserted into the other of the first and second plurality of mating electrical connectors to electrically connect and at least partially mount the sibling circuit board to the base circuit board.

18. The EMG circuit of claim 17:
wherein the plurality of first mating electrical connectors includes connectors on opposite ends of the face of the base circuit board; and
wherein the plurality of second mating electrical connectors includes connectors on opposite ends of the face of the sibling circuit board.

19. The EMG circuit of claim 18, wherein a first one of the first mating electrical connectors and the second mating electrical connectors comprises header pins, and a second one of the first mating electrical connectors and the second mating electrical connectors comprises header connections into which the header pins are inserted.

20. The EMG circuit of claim 10, wherein the following items are mounted and electrically connected to the sibling circuit board:
an analog-to-digital converter connected to the first EMG output signal, or another EMG output signal, from the base circuit board and configured to produce a corresponding digital EMG signal; and
a wireless transmitter configured to wirelessly transmit a signal that is based on the digital EMG signal to the client device.

21. The EMG circuit of claim 1:
wherein the operational amplifier of the difference circuit comprises an instrumentation amplifier;
wherein the offset removal circuit comprises a difference amplifier;
wherein the output circuit comprises an operational amplifier; and
wherein the rectification circuit comprises either a full wave or a half wave rectification circuit.

22. The electromyography (EMG) circuit of claim 1, comprising a single-polarity power source operable to provide a positive, non-zero voltage and a ground voltage to the EMG circuit, wherein the EMG output signal is a non-zero voltage that utilizes a ground voltage of the first single polarity power source as a baseline voltage, thereby enabling use of a full resolution of an output device into which the EMG output signal is fed.

23. An electromyography (EMG) circuit comprising:
a difference circuit configured to create an EMG signal based on a difference between two action potential voltages, wherein creation of the EMG signal introduces a voltage offset, not already present in the action potential voltages, that centers the EMG signal about a non-zero voltage;
a rectification circuit connected to the difference circuit and configured to rectify the EMG signal about the non-zero voltage to create a rectified EMG signal;
an offset removal circuit connected to the rectification circuit and configured to remove the voltage offset from the rectified EMG signal to create an adjusted EMG signal;
an output circuit connected to the offset removal circuit and configured to produce a first EMG output signal for a client device based on the adjusted EMG signal, wherein the first EMG output signal is an EMG envelope signal;
a circuit board that is a base circuit board and supports one or more of the difference circuit, rectification circuit, offset removal circuit, and output circuit, the circuit board having first and second openings that are spaced apart from each other on the circuit board, wherein the circuit board lies within a first plane;
a first electrode receptacle sized to receive a corresponding first electrode extension, the first electrode receptacle comprising an inlet having a centerline that extends through the first electrode receptacle and is perpendicular to the first plane;
a second electrode receptacle sized to receive a corresponding second electrode extension, the second electrode receptacle comprising an inlet having a centerline that extends through the second electrode receptacle and is perpendicular to the first plane; and
a sibling circuit board removably mounted to the base circuit board in a stacked configuration such that the circuit boards are parallel, face each other, are spaced apart from each other, and are electrically connected;
wherein the first and second electrode receptacles are snap-in electrode receptacles;
wherein the first electrode receptacle is embedded in the first opening, and the second electrode receptacle is embedded in the second opening;
wherein the sibling circuit board lies within a second plane that is parallel to the first plane when it is mounted to the base circuit board;
wherein the sibling circuit board comprises a third electrode receptacle sized to receive a third electrode extension, the third electrode receptacle comprising an inlet having a centerline that extends through the third electrode receptacle in a direction parallel to the second plane; and
wherein the third electrode extension comprises a Tip Sleeve (TS) connector or a Tip Ring Sleeve (TRS) connector that connects the two action potential voltages to the difference circuit.

24. The EMG circuit of claim 23, wherein the third electrode extension also connects a ground voltage of a subject from which the action potential voltages originate to the EMG circuit as a reference voltage.

25. A method implemented by an electromyography (EMG) circuit, comprising:
receiving action potential voltages from a plurality of electrodes;
creating, by an operational amplifier, an EMG signal based on a difference between action potential voltages of two of the plurality of electrodes, wherein said creating the EMG signal introduces a voltage offset, not already present in the action potential voltages, that centers the EMG signal about a non-zero voltage;
rectifying the EMG signal about the non-zero voltage to create a rectified EMG signal;
removing the voltage offset from the rectified EMG signal to create an adjusted EMG signal; and
producing a first EMG output signal for a client device based on the adjusted EMG signal, wherein the first EMG output signal is an EMG envelope signal.

26. The method of claim 25, wherein a power supply that powers the EMG circuit provides a voltage Vs to the EMG circuit, and wherein the non-zero voltage about which the EMG signal is rectified is Vs/2.

27. The method of claim 25, comprising:
providing the EMG signal, prior to rectification, as a second EMG output signal to the same or another client device.

28. The method of claim 25:
wherein the voltage offset that is introduced into the action potential voltages is a first voltage offset;
wherein the action potential voltages include a second voltage offset prior to the creating of the EMG signal; and
wherein the method comprises filtering the EMG signal to remove the second voltage offset from the EMG signal prior to the rectifying.

29. The method of claim 25, comprising:
adjusting a luminance of a light-emitting diode (LED) that is part of the EMG circuit based on an amplitude of the first EMG output signal, such that larger amplitudes output a higher luminance, and lower amplitudes output a lower luminance.

30. The method of claim 25, wherein the EMG circuit comprises a circuit board and wherein the two electrodes whose voltage difference is amplified include first and second electrodes, the method comprising:

connecting the first electrode to the circuit board by inserting a first electrode extension that is part of the first electrode into a first electrode receptacle in a snap-in connection, wherein the first electrode receptacle is embedded in a first opening of the circuit board; and connecting the second electrode to the circuit board by inserting a second electrode extension that is part of the second electrode into a different, second electrode receptacle in another snap-in connection, wherein the second electrode receptacle is embedded in a second opening of the circuit board;

wherein the first and second openings are spaced apart from each other on the circuit board and are aligned along a major axis of the circuit board.

31. The method of claim 30:
wherein the circuit board lies within a plane;
wherein the first electrode extension is inserted into the first electrode receptacle along a first axis that is perpendicular to the plane;
wherein the second electrode extension is inserted into the second electrode receptacle along a different, second axis that is also perpendicular to the plane;
the method comprising connecting a third electrode to the circuit board by inserting a third electrode extension, which is connected to the third electrode, into a third electrode receptacle on the circuit board along a third axis that is a central longitudinal axis that extends parallel to the plane;
wherein the third electrode connects a ground voltage of a subject from which the action potential voltages originate to the EMG circuit as a reference voltage.

32. The method of claim 30, wherein the circuit board is a base circuit board, the method comprising:
mounting a sibling circuit board to the base circuit board in a stacked configuration such that the circuit boards are parallel, face each other, and are spaced apart from each other;
wherein the mounting comprises electrically connecting the sibling circuit board to the base circuit board.

33. The method of claim 32, wherein mounting the sibling circuit board to the base circuit board comprises:
aligning the base and sibling circuit boards such that the circuit boards face each other, and such that a first plurality of mating electrical connectors that extend outwardly in a perpendicular direction away from the base circuit board and a second plurality of the mating electrical connectors that extend outwardly in a perpendicular direction away from the sibling circuit board extend towards each other; and inserting one of the first and second plurality of mating electrical connectors into the other of the first and second plurality of mating electrical connectors to electrically connect and at least partially mount the sibling circuit board to the base circuit board.

34. The method of claim 33, wherein a first one of the first and second plurality of mating electrical connectors comprises header pins, and a second one of the first and second plurality of mating electrical connectors comprises header connections sized for insertion of the header pins.

35. The method of claim 32, comprising:
mounting and electrically connecting an energy storage device to the sibling circuit board; and
powering the base circuit board and the sibling circuit board from the energy storage device.

36. The method of claim 32, wherein a plurality of light-emitting diodes (LEDs) and an LED driver circuit are mounted and electrically connected to the sibling circuit board, the method comprising:
applying the first EMG output signal to the LED driver circuit, such that an amplitude of the first EMG output signal controls a quantity of the LEDs that are illuminated by the LED driver circuit.

37. The method of claim 25, comprising:
passing the first EMG output signal, or another EMG output signal of the EMG circuit, through an analog-to-digital converter to create a digital EMG signal; and
wirelessly transmitting a signal based on the digital EMG signal to a client device.

38. The method of claim 25:
wherein the EMG circuit comprises a base circuit board that performs at least some of the receiving, creating, rectifying, removing, and producing;
wherein the two electrodes whose voltage difference is amplified include first and second electrodes; and
wherein the method comprises:
mounting a sibling circuit board to the base circuit board in a stacked configuration such that the circuit boards are parallel, face each other, and are spaced apart from each other, the mounting at least partially implemented via a plurality of mating connectors, wherein the sibling circuit board lies in a plane, the mounting comprising electrically connecting the sibling circuit board to the base circuit board via the mating connectors; and
inserting an electrode extension into an electrode receptacle on the sibling circuit board in a direction parallel to the plane, wherein the electrode extension comprises a Tip Sleeve (TS) connector or a Tip Ring Sleeve (TRS) connector that connects the first and second electrodes to the EMG circuit.

* * * * *